US006951867B2

(12) United States Patent (10) Patent No.: US 6,951,867 B2
Katsu et al. (45) Date of Patent: Oct. 4, 2005

(54) N-SUBSTITUTED PIPERIDINYL-IMIDAZOPYRIDINE COMPOUNDS AS 5-HT₄ RECEPTOR MODULATORS

(75) Inventors: Yasuhiro Katsu, Taketoyo-cho (JP); Kana Kon-I, Taketoyo-cho (JP); Mikio Morita, Taketoyo-cho (JP); Hirohide Noguchi, Taketoyo-cho (JP); Chikara Uchida, Taketoyo-cho (JP)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/667,182

(22) Filed: Sep. 17, 2003

(65) Prior Publication Data

US 2004/0127514 A1 Jul. 1, 2004

Related U.S. Application Data

(60) Provisional application No. 60/412,426, filed on Sep. 20, 2002.

(51) Int. Cl.⁷ .................. A61K 31/437; C07D 471/04; A61P 1/04

(52) U.S. Cl. .................. 514/300; 514/233.2; 514/303; 546/121; 546/112; 544/127

(58) Field of Search .................. 546/121; 514/300, 514/233.2; 544/127

(56) References Cited

U.S. PATENT DOCUMENTS

| | | | | |
|---|---|---|---|---|
| 5,137,893 A | 8/1992 | Becker et al. | ............... | 514/293 |
| 5,196,547 A | 3/1993 | Becker et al. | ............... | 548/453 |
| 5,219,850 A | 6/1993 | Becker et al. | ............... | 514/214 |
| 5,260,303 A | 11/1993 | Becker et al. | ............... | 514/300 |
| 5,434,161 A | 7/1995 | Becker et al. | ............... | 514/300 |
| 5,591,749 A | 1/1997 | Becker et al. | ............... | 514/300 |
| 5,604,239 A | 2/1997 | Becker et al. | ............... | 514/300 |
| 6,624,162 B2 * | 9/2003 | Uchida et al. | ........... | 514/233.2 |

FOREIGN PATENT DOCUMENTS

| | | |
|---|---|---|
| EP | 0274867 | 7/1988 |
| EP | 0504679 | 9/1992 |
| JP | H01258674 | 10/1989 |
| JP | H02643274 | 10/1989 |
| JP | 2001006877 | 1/2001 |
| WO | WO9215593 | 9/1992 |
| WO | WO9408998 | 4/1994 |
| WO | WO9605166 | 2/1996 |
| WO | WO9727852 | 8/1997 |
| WO | WO9738665 | 10/1997 |
| WO | WO9950247 | 10/1999 |
| WO | WO0105763 | 1/2001 |

OTHER PUBLICATIONS

Barnes et al. Neuropharmacology 38(1999) 1083–1085, 1118–1125.*

Dumuis, et al., "A 5-HT receptor in the central nervous system, positively coupled with adenylate cyclase, is antagonized by ICS 205 930", *European Journal of Pharmacology*, 146 (1988), 187–188.

Dumuis, et al., "The gastrointestinal prokinetic benzamide derivatives are agonists at the non-classical 5-HT receptor (5-HT₄) positively coupled to adenylate cyclase in neurons", *Naunyn–Schmiedeberg's Arch. Pharmacol.* (1989) 340: 403–410.

Bockaert, et al., "The 5-HT4 receptor: a place in the sun", *TiPs*, 1992, 13, 141–145.

Ford, A.P.D.W., et al., "The 5-HT₄ Receptor", *Med. Res. Rev.*, 1993, 13, 633–662.

Gullikson, G.W., et al., "Gastrointestinal Motility Responses to the S and R Enantiomers of Zacopride, a 5-HT4 Agonist and 5-HT3 Antagonist", *Drug Dev. Res.*, 1992, 26, 405–417.

(Continued)

*Primary Examiner*—Evelyn Mei Huang
(74) *Attorney, Agent, or Firm*—Gregg C. Benson; Frank W. Forman

(57) ABSTRACT

This invention provides a compound of the formula (I):

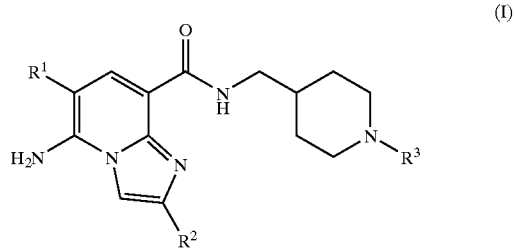

or a pharmaceutically acceptable salt, amide or ester thereof, wherein $R^1$ represents a hydrogen atom or a halogen atom; $R^2$ represents a hydrogen atom, etc.; $R^3$ represents an alkyl group having from 1 to 10 carbon atoms; said alkyl group of $R^3$ is substituted by at least one substituent selected from the group consisting of substituents α; said substituents α is aryl, hydroxy, oxo, etc.; said aryl having 6 to 10 carbon atoms; said aryl is unsubstituted or substituted by at least one alkyl group having from 1 to 6 carbon atoms; said heterocyclic and the heterocyclic moiety of said heterocycliccarbonyl, both of substituents α, are 5- to 10-membered cyclic groups containing from 1 to 4 heteroatoms selected from the group consisting of nitrogen atoms, oxygen atoms and sulfur atoms These compounds have 5-HT₄ receptor binding activity, and thus are useful for the treatment of gastroesophageal reflux disease, non-ulcer dyspepsia, functional dyspepsia, irritable bowel syndrome or the like in mammalian, especially humans. This invention also provides a pharmaceutical composition comprising the above compound.

20 Claims, No Drawings

OTHER PUBLICATIONS

Eglen, et al., "Central 5–HT4 receptors", *TiPs*, 1995, 16, 391–398.

Bockaert, Jr., et al., "5–HT$_4$ Receptors Potential Therapeutic Implications in Neurology and Psychiatry", *CNS Drugs*, 1, 6–14 (1994).

Romanelli, M.N., et al., "Synthesis and Biological Activity of a Series of Aryl Tropanyl Esters and Amides Chemically Related to 1H–Indole–3–carboxylic Acid endo 8–Methyl–8–azabicyclo[3.2.1]oct–3–yl Ester" *Arzneimittel Forschung Drug Research*, 1993, 43(II), 913–918.

Kaumann, A., et al., ., "A 5–HT$_4$–like receptor in human right atrium", *Naunyn–Schmiedeberg's Arc., Pharmacol.* (1991), 344, 150–159.

Finlayson, K., et al., "[$^3$H]Dofetilide binding to HERG transfected membranes: a potential high throughput preclinical screen", *European Journal of Pharmacology*, 430, (2001), 147–148.

Mutterer, et al., "Hatogenierte Pyridine V. Fluorierte und bromierte Pyridinverbindugen", *Helv. Chim. Acta*, (1976), 59, 229–235.

Barlow, et al., "Diels–Alder reactions of trochloro–1,2,4–triazine: intramolecular additions with 1,5 and 1,6 dienes", *J. Chem. Soc., Perkin Trans. I*, (1996), 519–524.

Lantos, et al., "Novel Cage Compounds from Inter–intra–molecular Diels–Alder Reactions of 1,2,4–Triazines with Cyclo–octa–1,5–diene", *J. Chem. Soc., Chem. Commun.* (1998), 1482–1483.

Feibush, et al., "Chiral Separation of Heterocyclic Drugs by HPLC: Solute–Stationary Phase Base–Pair Interactions", *J. Am. Chem. Soc.*, (1986), 108(12), 3310–3318.

G.S. Baxter, et al., "5–Hydroxytryptamine$_4$ receptors mediate relaxation of the rat oesophageal tunica muscularis mucosae", *Naunyn–Schmiedeberg's Arch. Pharmacol.*, (1991), 343, 439–446.

Yukiko Mine, et al, "Comparison of Effect of Mosapride Citrate and Existing 5–HT$_4$ Receptor Agonists on Gastrointestinal Motility In Vivo and In Vitro", *JPET*, (1997) 283: 1000–1008.

Reeves, J.J., et al., "Investigation into the 5–hydroxytryptamine receptor mediating smooth muscle relaxation in the rat oesophagus", *British Journal of Pharmacology*, (1991) 103: 1067–1072.

Z. Zhou, et al., "Properties of HERG Channels Stably Expressed in HEK 293 Cells Studied at Physiological Temperature", *Biophysical Journal*, 74, 230–241.

M.C. Coldwell, et al., "The Synthesis and Dopamine D$_2$ and Serotonin 5–HT$_3$ Receptor Affinity of 3–Aza Analogues (Pyridyl) of 4–Amino–5–chloro–2–methoxybenzamides", *Biorg. Med. Chem. Lett.*, vol. 5, No. 1, 39–42 (1995).

D. Subhas Bose, et al., "Boron Trifluoride Promated Cleavage of Benzyl Carbamates", *Tetrahedron Lett.*, vol. 31, No. 47, 6903–6906, 1990.

Prugh, et al., A Simple Method of Protecting a Secondary Amine with tert Butyloxycarbonyl (BOC) in the Presence of a Primary Amine, *Synth. Commun.*, 1992, 22, 2357–60.

G. Bertram, et al., "Total Synthesis of (±)–Strobilurin E", *Tetrahedron Lett.*, vol. 37, No. 44, 7955–7958, 1996.

W.C. Lumma, Jr., et al., "Condensation of Unsymmetrical Aliphatic Ketones with Formaldehyde in Trilluoroacetic Acid", *J. Org. Chem.*, vol. 35, No. 7, 1970, 2391–2393.

A. Otha, et al., "Stereoselective Synthesis of Spicy Components in Peppers", *Heterocycles*, 1991, vol. 32, 965–73.

B.G. Hazra, et al., "An Improved Procedure for the Dichloroacetylation of Primary and Secondary Amines", *Org. Prep. Proced. Int.*, 1989, 21, 355–358.

G. Mattalia, et al., "Synthesis of New Derivatives of the 4,5–Diphenyloxazole Series", *Il Farmaco, Ed. Sci.*, 1976, 31, 457–67.

Lopez–Rodriguez, et al., "Benzimidazole Derivatives. Part 1: Synthesis and Structure–Activity Relationships of New Benzimi9dazole–4–carboxamides and Carboxylates as Potent and Selective 5–HT4 Receptor Antagonists", *Bioorganic & Medicinal Chemistry*, 7 (1999), 2271–2281.

Katz, J., et al., "Action des isopropyl–9 et tertiobutyl–9 bora–9 bicyclo (3.3.1)nonanes sur quelques cétones α–bromées. Synthése de cétones substituées", *Bull. Soc. Chim. Fr.*, 1997,683–687.

Chem. Abstr., 1963, 58, 5570f.

\* cited by examiner

N-SUBSTITUTED PIPERIDINYL-IMIDAZOPYRIDINE COMPOUNDS AS 5-HT₄ RECEPTOR MODULATORS

RELATED APPLICATIONS

This application claims benefit of priority under 35 U.S.C 119(e) to U.S. Provisional Application No. 60/412,426 filed on Sep. 20, 2002, which is herein incorporated in its entirety by reference.

TECHNICAL FIELD

This invention relates to novel imidazopyridine compounds. These compounds have $5\text{-HT}_4$ receptor agonist binding activity, and thus are useful for the treatment of or prevention of gastroesophageal reflux disease, gastrointestinal disease, gastric motility disorder, non-ulcer dyspepsia, functional dyspepsia, irritable bowel syndrome, constipation, dyspepsia, esophagitis, gastroesophageral disease, nausea, central nervous system disease, alzheimers disease, cognitive disorder, emesis, migraine, neurological disease, pain, ischaemic stroke, anxiety, cardiovascular disorder or the like, in mammalian, especially human. The present invention also relates to a pharmaceutical composition comprising the above compounds.

BACKGROUND ART

Serotonin (5-HT) receptors are known to have a plurality of subtypes such as $5\text{-HT}_1$, $5\text{-HT}_2$, $5\text{-HT}_3$ and $5\text{-HT}_4$. These $5\text{-HT}_4$ receptors are disclosed in, for example, European Journal of Pharmacology 146 (1988), 187–188, and Naunyn-Schmiedeberg's Arch. Pharmacol. (1989) 340:403–410.

$5\text{-HT}_4$ receptor modulators (e.g., agonists and antagonists) are found to be useful for the treatment of a variety of diseases such as gastroesophageal reflux disease, gastrointestinal disease, gastric motility disorder, non-ulcer dyspepsia, functional dyspepsia, irritable bowel syndrome, constipation, dyspepsia, esophagitis, gastroesophageral disease, nausea, central nervous system disease, alzheimers disease, cognitive disorder, emesis, migraine, neurological disease, pain, and cardiovascular disorders such as cardiac failure and heart arryhthmia (See TiPs, 1992, 13, 141; Ford A. P. D. W. et al., Med. Res. Rev., 1993, 13, 633; Gullikson G. W. et al., Drug Dev. Res., 1992, 26, 405; Richard M. Eglen et al, TiPS, 1995, 16, 391; Bockaert J. Et al., CNS Drugs, 1, 6; Romanelli M. N. et al., Arzheim Forsch./Drug Res., 1993, 43, 913; Kaumann A. et al., Naunyn-Schmiedeberg's. 1991, 344, 150; and Romanelli M. N. et al., Arzheim Forsch./Drug Res., 1993, 43, 913).

A variety of imidazopyridine compounds have been known as 5HT receptor antagonists or agonists. For example, Japanese Patent Publication Laid-Open No. H01-258,674 and H02-643,274 disclose imidazopyridine compounds as 5HT receptor antagonists. WO 96/05166 discloses imidazopyridine compounds as $5\text{HT}_4$ agonists. WO92/15593; U.S. Pat. Nos. 5,260,303; 5,604,239; 5,591,749; 5,219,850; 5,434,161; 5,137,893; 5,196,547; and EP 504679 describe a variety of imidazopyridine compounds as $5\text{HT}_3$ receptor antagonists. WO94/08998 discloses imidazopyridine compounds as $5\text{HT}_4$ receptor antagonists.

Also, imidazopyridine compounds synthesized for different uses are described in JP2001/6877; WO01/5763; WO 99/50247; WO 97/27852, WO 9738665 and EP 274867.

It would be desirable if there were provided $5\text{HT}_4$ receptor agonists which have more $5\text{HT}_4$ receptor agonist activities.

A variety of imidazopyridine $5\text{-HT}_4$ receptor modulators compounds were disclosed in U.S. application Ser. No. 60/343,371, filed on Oct. 22, 2001.

QT prolongation is known to have a potential liability to produce fatal cardiac arrhythmias of Torsades de Pointes (TdP). The ability to prolong the cardiac action potential duration was identified as being due to an action at the HERG potassium channel. For example, drugs withdrawn from the market due to QT prolongation, such as Cisapride and Terfenadine, are known to be potent HERG potassium channel blocker (Expert Opinion of Pharmacotherapy.; 2, pp. 947–973, 2000). Therefore, it would be desirable if there were provided a novel 5HT4 selective agonist useful for the treatment of a variety of diseases such as gastroesophageal reflux disease, gastrointestinal disease, gastric motility disorder, non-ulcer dyspepsia, functional dyspepsia, irritable bowel syndrome, constipation, dyspepsia, esophagitis, gastroesophageral disease, nausea, central nervous system disease, alzheimers disease, cognitive disorder, emesis, migraine, neurological disease, pain, and cardiovascular disorders such as cardiac failure and heart arrhythmia, by systemic administration and with reduced inhibitory activity at HERG potassium channel.

BRIEF DISCLOSURE OF THE INVENTION

It has now been found that compounds in the present invention are $5\text{HT}_4$ selective agonists useful for the treatment of a variety of diseases such as gastroesophageal reflux disease, gastrointestinal disease, gastric motility disorder, non-ulcer dyspepsia, functional dyspepsia, irritable bowel syndrome, constipation, dyspepsia, esophagitis, gastroesophageral disease, nausea, central nervous system disease, alzheimers disease, cognitive disorder, emesis, migraine, neurological disease, pain, and cardiovascular disorders such as cardiac failure and heart arrhythmia, by systemic administration and with reduced inhibitory activity at HERG channel. Inhibitory activity at HERG channel was estimated from affinity for HERG type potassium channel was investigated by checking [³H]dofetilide binding, which can predict inhibitory activity at HERG channel (Eur. J. Pharmacol., 430, pp147–148, 2001). Selected compounds with low [³H] dofetilide binding activity were evaluated in $I_{HERG}$ assay to check activity at HERG channel. Introducing substituent(s) to an alkyl group attached to nitrogen atom in piperidine ring contributed to potent $5\text{-HT}_4$ receptor agonist activities with reduced inhibitory activity at HERG channel. The compounds of the present invention may show less toxicity, good absorption, distribution and less drug-drug interaction, and have metabolic stability.

The present invention provides a compound of the following formula (I):

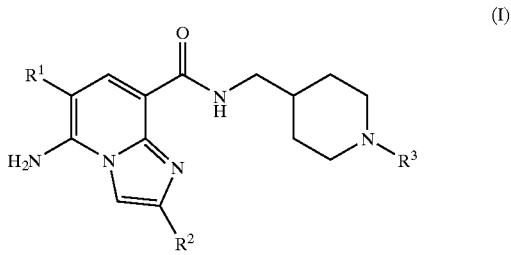

wherein
R¹ represents a hydrogen atom or a halogen atom;
R² represents a hydrogen atom, an alkyl group having from 1 to 6 carbon atoms, an aminocarbonyl group, or mono- or di-alkylaminocarbonyl group having from 1 to 6 carbon atoms;

R³ represents an alkyl group having from 1 to 10 carbon atoms;
said alkyl group in R³ is substituted by at least one substituent selected from the group consisting of substituents α, defined below;
said substituents α is selected from the group consisting of aryl groups defined below, hydroxy groups, oxo groups, aminocarbonyl groups, mono- or di-alkylaminocarbonyl groups having from 1 to 6 carbon atoms, alkylsulfonylamino groups having from 1 to 6 carbon atoms, heterocyclic groups defined below, heterocycliccarbonyl groups and a cycloalkyl group having from 3 to 8 carbon atoms;
said aryl groups have 6 to 10 carbon atoms;
said aryl groups are unsubstituted or substituted by at least one alkyl group having from 1 to 6 carbon atoms;
said heterocyclic groups and the heterocyclic moiety of said heterocycliccarbonyl groups are 5- to 10-membered cyclic groups containing from 1 to 4 heteroatoms selected from the group consisting of sulfur atoms, oxygen atoms and nitrogen atoms;
or a pharmaceutically acceptable amide of such compound, or a pharmaceutically acceptable ester of such compound, or a pharmaceutically acceptable salt thereof.

The present invention provides a compound of the formula (I):

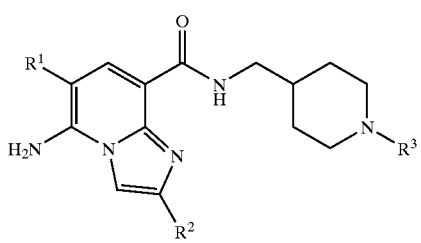

(I)

wherein
R¹ represents a hydrogen atom or a halogen atom;
R² represents a hydrogen atom, an alkyl group having from 1 to 6 carbon atoms, an aminocarbonyl group, or mono- or di-alkylaminocarbonyl group having from 1 to 6 carbon atoms;
R³ represents an alkyl group having from 1 to 10 carbon atoms;
said alkyl group in R³ is substituted by at least one substituent selected from the group consisting of substituents α, defined below;
said substituents α is selected from the group consisting of aryl groups defined below, hydroxy groups, oxo groups, aminocarbonyl groups, mono- or di-alkylaminocarbonyl groups having from 1 to 6 carbon atoms, alkylsulfonylamino groups having from 1 to 6 carbon atoms, heterocyclic groups defined below, heterocycliccarbonyl groups and a cycloalkyl group having from 3 to 8 carbon atoms;
said aryl groups have 6 to 10 carbon atoms;
said aryl groups are unsubstituted or substituted by at least one alkyl group having from 1 to 6 carbon atoms;
said heterocyclic groups and the heterocyclic moiety of said heterocycliccarbonyl groups are 5- to 10-membered cyclic groups containing from 1 to 4 heteroatoms selected from the group consisting of sulfur atoms, oxygen atoms and nitrogen atoms;
or a pharmaceutically acceptable ester of such compound, or a pharmaceutically acceptable salt thereof.

The N-substituted piperidinyl-imidazopyridine compounds of this invention have 5-HT₄ receptor agonistic activities, and are thus useful for the treatment or prevention of disease conditions mediated by 5-HT₄ receptor activities with reduced inhibitory activity at HERG channel.

Thus, the present invention provides a pharmaceutical composition for the treatment of disease conditions mediated by 5-HT₄ receptor activities, in a mammalian subject, which comprises administering to said subject a therapeutically effective amount of a compound of formula (I), a pharmaceutically acceptable amide of the compound, or a pharmaceutically acceptable ester of the compound, or a pharmaceutically acceptable salt thereof.

Further, the present invention also provides a pharmaceutical composition for the treatment of gastroesophageal reflux disease, gastrointestinal disease, gastric motility disorder, upper gut motility disorder, non-ulcer dyspepsia, functional dyspepsia, irritable bowel syndrome, constipation, dyspepsia, esophagitis, gastroesophageral disease, nausea, central nervous system disease, alzheimers disease, cognitive disorder, emesis, migraine, neurological disease, pain, ischaemic stroke, anxiety, cardiovascular disorders such as cardiac failure and heart arryhthmia, or the like, which comprises a therapeutically effective amount of the imidazopyridine compound of formula (I), a pharmaceutically acceptable amide of the compound, or a pharmaceutically acceptable ester of the compound, or a pharmaceutically acceptable salt thereof together with a pharmaceutically acceptable carrier.

Also, the present invention provides a method for the treatment of disease conditions mediated by 5-HT₄ receptor activities, in a mammalian subject, which comprises administering to said subject a therapeutically effective amount of a compound of formula (I), a pharmaceutically acceptable amide of the compound, or a pharmaceutically acceptable ester of the compound, or a pharmaceutically acceptable salt thereof. Further, the present invention provides a method for the treatment of the disease conditions as mentioned above. Furthermore, the present invention provides use of the compound of formula (I), a pharmaceutically acceptable amide of the compound, or a pharmaceutically acceptable ester of the compound, or a pharmaceutically acceptable salt thereof in the manufacture of a medicament for the treatment or prevention of disease conditions mediated by 5-HT₄ receptor activity, in a mammalian subject. The conditions mediated by 5-HT₄ receptor activity are those diseases or disorders described as above.

DETAILED DESCRIPTION OF THE INVENTION

As used herein, unless indicated otherwise, the article "a" or "an" refers to both the singular and plural form of the object to which it refers.

As used herein, the term "halogen" means fluoro, chloro, bromo and iodo, preferably fluoro or chloro.

As used herein, the term "alkyl" means straight or branched chain saturated radicals, including, but not limited to methyl, ethyl, n-propyl, isopropyl, n-butyl, iso-butyl, secondary-butyl, tertiary-butyl.

As used herein, the term "aryl" means a monocyclic or bicyclic aromatic carbocyclic ring of 6 to 14 carbon atoms, preferably 6 to 10 carbon atoms including, but not limited to, phenyl, naphthyl, indanyl, preferably phenyl and naphthyl.

The term "cycloalkyl", as used herein, means a saturated carbocyclic radical ring of 3 to 8 carbon atoms, including, but not limited to, cyclopropyl, cyclobutyl, cyclohexyl, cycloheptyl, cyclooctyl, cyclononyl, cyclodecyl and the like.

As used herein, the term "heterocyclic" means a 5- to 10-membered monocyclic or bicyclic ring which may be saturated, partially unsaturated, or aromatic, and which consists of carbon atoms and from 1 to 4 heteroatoms independently selected from the group consisting of N, O and S. Examples of the heterocyclics include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H, 6H-1,5,2-dithiazinyl, thiophenyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4a H-carbazole, carbazole, beta-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Preferable heterocyclic groups include piperidino, morpholino, thiamorpholino, pyrrolidino, pyrazolino, pyrazolidino, pyrazoryl, piperazinyl, furyl, thienyl, oxazolyl, tetrazolyl, thiazolyl, imidazolyl, imidazolinyl, pyrazolyl, pyridyl, pyrimidinyl, pyrrolyl, pyrrolidinyl, piperidinyl, morpholinyl and quinolyl.

As used herein, the term "heterocycliccarbonyl" means a heterocyclic-C(=O)— group where heterocyclic is as defined above.

Where the compounds of formula (I) contain hydroxy groups, they may form esters. Examples of such esters include esters with a hydroxy group and esters with a carboxy group. The ester residue may be an ordinary protecting group or a protecting group which can be cleaved in vivo by a biological method such as hydrolysis. The nitrogen atom of piperidine group of a compound of formula (I) can form an amide.

The term "ordinary protecting group" means a protecting group, which can be cleaved by a chemical method such as hydrogenolysis, hydrolysis, electrolysis or photolysis.

The term "protecting group which can be cleaved in vivo by a biological method such as hydrolysis" means a protecting group which is cleaved in vivo by a biological method such as hydrolysis and forms a free acid or salt thereof. Whether a compound is such a derivative or not can be determined by administering it by intravenous injection to an experimental animal, such as a rat or mouse, and then studying the body fluids of the animal to determine whether or not the compound or a pharmaceutically acceptable salt thereof can be detected.

Preferred examples of such ordinary protecting groups for an ester of a hydroxy group include: lower aliphatic acyl groups, for example: alkanoyl groups, such as the formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl and henicosanoyl groups; halogenated alkylcarbonyl groups, such as the chloroacetyl, dichloroacetyl, trichloroacetyl, and trifluoroacetyl groups; alkoxyalkylcarbonyl groups, such as the methoxyacetyl group; and unsaturated alkylcarbonyl groups, such as the acryloyl, propioloyl, methacryloyl, crotonoyl, isocrotonoyl and (E)-2-methyl-2-butenoyl groups; more preferably, the lower aliphatic acyl groups having from 1 to 6 carbon atoms; aromatic acyl groups, for example: arylcarbonyl groups, such as the benzoyl, α-naphthoyl and β-naphthoyl groups; halogenated arylcarbonyl groups, such as the 2-bromobenzoyl and 4-chlorobenzoyol groups; lower alkylated arylcarbonyl groups, such as the 2,4,6-trimethylbenzoyl and 4-toluoyl groups; lower alkoxylated arylcarbonyl groups, such as the 4-anisoyl group; nitrated arylcarbonyl groups, such as the 4-nitrobenzoyl and 2-nitrobenzoyl groups; lower alkoxycarbonylated arylcarbonyl groups, such as the 2-(methoxycarbonyl)benzoyl group; and arylated arylcarbonyl groups, such as the 4-phenylbenzoyl group; alkoxycarbonyl groups, for example: lower alkoxycarbonyl groups, such as the methoxycarbonyl, ethoxycarbonyl, propoxycarbonyl, butoxycarbonyl, sec-butoxycarbonyl, t-butoxycarbonyl and isobutoxycarbonyl groups; and halogen- or tri(lower alkyl)silyl-substituted lower alkoxycarbonyl groups, such as the 2,2,2-trichloroethoxycarbonyl and 2-trimethylsilylethoxycarbonyl groups; tetrahydropyranyl or tetrahydrothiopyranyl groups, such as: tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl groups; tetrahydrofuranyl or tetrahydrothiofuranyl groups, such as: tetrahydrofuran-2-yl and tetrahydrothiofuran-2-yl groups; silyl groups, for example: tri(lower alkyl)silyl groups, such as the trimethylsilyl, triethylsilyl, isopropyldimethylsilyl, t-butyldimethylsilyl, methyldiisopropylsilyl, methyldi-t-butylsilyl and triisopropylsilyl groups; and tri(lower alkyl) silyl groups substituted by 1 or 2 aryl groups, such as the diphenylmethylsilyl, diphenylbutylsilyl, diphenylisopropylsilyl and phenyldiisopropylsilyl groups; alkoxymethyl groups, for example: lower alkoxymethyl groups, such as the methoxymethyl, 1,1-dimethyl-1-methoxymethyl, ethoxymethyl, propoxymethyl, isopropoxymethyl, butoxymethyl and t-butoxymethyl groups; lower alkoxylated lower alkoxymethyl groups, such as the 2-methoxyethoxymethyl group; and halo(lower alkoxy) methyl groups, such as the 2,2,2-trichloroethoxymethyl and bis(2-chloroethoxy)methyl groups; substituted ethyl groups, for example: lower alkoxylated ethyl groups, such as the 1-ethoxyethyl and 1-(isopropoxy)ethyl groups; and halogenated ethyl groups, such as the 2,2,2-trichloroethyl group; aralkyl groups, for example: lower alkyl groups substituted by from 1 to 3 aryl groups, such as the benzyl, α-naphthylmethyl, β-naphthylmethyl, diphenylmethyl, triphenylmethyl, α-naphthyldiphenylmethyl and 9-anthrylmethyl groups; and lower alkyl groups substituted by from 1 to 3 substituted aryl groups, where one or more of the aryl groups is substituted by one or more lower alkyl, lower alkoxy, nitro, halogen or cyano substituents, such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl groups; alkenyloxycarbonyl groups: such as the vinyloxycarbonyl and aryloxycarbonyl groups; and aralkyloxycarbonyl groups in which the aryl ring may be substituted by 1 or 2 lower alkoxy or nitro groups: such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

The term "protecting group", as used herein, means a hydroxy or amino protecting group which is selected from typical hydroxy or amino protecting groups described in Protective Groups in Organic Synthesis edited by T. W. Greene et al. (John Wiley & Sons, 1991);

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

In the compounds of formula (I), $R^1$ represents preferably a hydrogen atom or a chlorine atom, more preferably a chlorine atom.

In the compounds of formula (I), $R^2$ represents preferably represents an alkyl group having from 1 to 6 carbon atoms, an aminocarbonyl group, or mono- or di-alkylaminocarbonyl group having from 1 to 6 carbon atoms; more preferably an alkyl group having from 1 to 6 carbon atoms; and most preferably a methyl group or an ethyl group.

In the compounds of formula (I), $R^3$ is preferably an alkyl group having from 1 to 8 carbon atoms;

said alkyl group in $R^3$ is substituted by at least one substituent selected from the group consisting of substituents α, defined below;

said substituents α is selected from the group consisting of aryl groups, hydroxy groups, oxo groups, aminocarbonyl groups, mono- or di-alkylaminocarbonyl groups having from 1 to 6 carbon atoms, alkylsulfonylamino groups having from 1 to 6 carbon atoms, heterocyclic groups defined below, heterocycliccarbonyl groups and a cycloalkyl group having from 3 to 8 carbon atoms;

said heterocyclic groups and the heterocyclic moiety of said heterocycliccarbonyl groups are 5- to 7-membered cyclic groups containing from 1 to 3 heteroatoms selected from the group consisting of sulfur atoms, oxygen atoms and nitrogen atoms; more preferably an alkyl group having from 1 to 10 carbon atoms;

said alkyl group in $R^3$ is substituted by at least one substituent selected from the group consisting of substituents α, defined below;

said substituents α are selected from the group consisting of aryl groups, hydroxy groups, oxo groups, alkylsulfonylamino groups having from 1 to 6 carbon atoms and heterocycliccarbonyl groups;

said heterocyclic moiety of said heterocycliccarbonyl groups are selected from the group consisting of piperidinyl and morpholinyl.

Preferred individual compounds of this invention are:

5-amino-6-chloro-N-{[1-(3,3-dimethyl-2-oxobutyl) piperidin-4-yl]methyl}-2-methylimidazo[1,2-a]pyridine-8-carboxamide;

5-amino-6-chloro-N-{[1-(2-hydroxy-3,3-dimethylbutyl) piperidin-4-yl]methyl}-2-methylimidazo[1,2-a]pyridine-8-carboxamide;

5-amino-6-chloro-2-ethyl-N-{[1-(3-morpholin-4-yl-3-oxopropyl)piperidin-4-yl]methyl}imidazo[1,2-a]pyridine-8-carboxamide;

5-amino-6-chloro-2-ethyl-N-{[1-(2-morpholin-4-yl-2-oxoethyl)piperidin-4-yl]methyl}imidazo[1,2-a]pyridine-8-carboxamide;

5-amino-6-chloro-N-{[1-(3,3-dimethyl-2-oxo-2-butyl) piperidin-4-yl]methyl}-2-ethylimidazo[1,2-a]pyridine-8-carboxamide;

5-amino-6-chloro-2-ethyl-N-{[1-(2-[(methylsulfonyl) amino]ethyl))piperidin-4-yl]]]methyl]imidazo[1,2-a] pyridine-8-carboxamide;

5-amino-6-chloro-2-ethyl-N-{[(1-2-hydroxy-2-methylpropyl)piperidin-4-yl]methyl}imidazo[1,2-a] pyridine-8-carboxamide;

5-amino-6-chloro-N-{[1-(2-hydroxy-2-methylpropyl) piperidin-4-yl]methyl}-2-methylimidazo[1,2-a]pyridine-8-carboxamide;

5-amino-6-chloro-2-ethyl-N-{[1-(4-hydroxy-3,3-dimethyl-2-oxobutyl)piperidin-4-yl]methyl}imidazo[1,2-a] pyridine-8-carboxamide;

5-amino-6-chloro-2-ethyl-N-{[1-(2-hydroxybutyl) piperidin-4-yl]methyl}imidazo[1,2-a]pyridine-8-carboxamide, half oxalate salt; and 5-amino-6-chloro-2-ethyl-N-{[1-(2-oxy-2-piperidin-1-ylethyl)piperidin-4-yl]methyl}imidazo[1,2-a]pyridine-8-carboxamide;

or an ester of such compound, or a salt thereof.

Most preferred individual compounds of this invention are:

5-amino-6-chloro-N-{[1-(3,3-dimethyl-2-oxo-2-butyl) piperidin-4-yl]methyl}-2-ethylimidazo[1,2-a]pyridine-8-carboxamide;

5-amino-6-chloro-2-ethyl-N-{[1-(2-[(methylsulfonyl) amino]ethyl))piperidin-4-yl]]]methyl]imidazo[1,2-a] pyridine-8-carboxamide;

5-amino-6-chloro-2-ethyl-N-{[(1-2-hydroxy-2-methylpropyl)piperidin-4-yl]methyl}imidazo[1,2-a] pyridine-8-carboxamide;

5-amino-6-chloro-N-{[1-(2-hydroxy-2-methylpropyl) piperidin-4-yl]methyl}-2-methylimidazo[1,2-a]pyridine-8-carboxamide;

5-amino-6-chloro-2-ethyl-N-{[1-(4-hydroxy-3,3-dimethyl-2-oxobutyl)piperidin-4-yl]methyl}imidazo[1,2-a] pyridine-8-carboxamide;5-amino-6-chloro-2-ethyl-N-{[1-(2-hydroxybutyl)piperidin-4-yl]methyl}imidazo[1,2-a]pyridine-8-carboxamide, half oxalate salt; and 5-amino-6-chloro-2-ethyl-N-{[1-(2-oxy-2-piperidin-1-ylethyl)piperidin-4-yl]methyl}imidazo[1,2-a]pyridine-8-carboxamide;

or an ester of such compound, or a salt thereof.

General Synthesis

The imidazopyridine compounds of formula (I) of this invention may be prepared by a variety of synthetic methods. Unless indicated otherwise, all variables (e.g. $R^1$, $R^2$ and $R^3$) are each as set forth herein. For example, the imidazopyridine compounds of formula (1), may be prepared by saponification of a carboxylate compound (II) to obtain a corresponding carboxylic acid compound (III), followed by a coupling reaction of the compound (III) with an amine compound (IV), as indicated in the following Scheme 1.

Scheme 1:

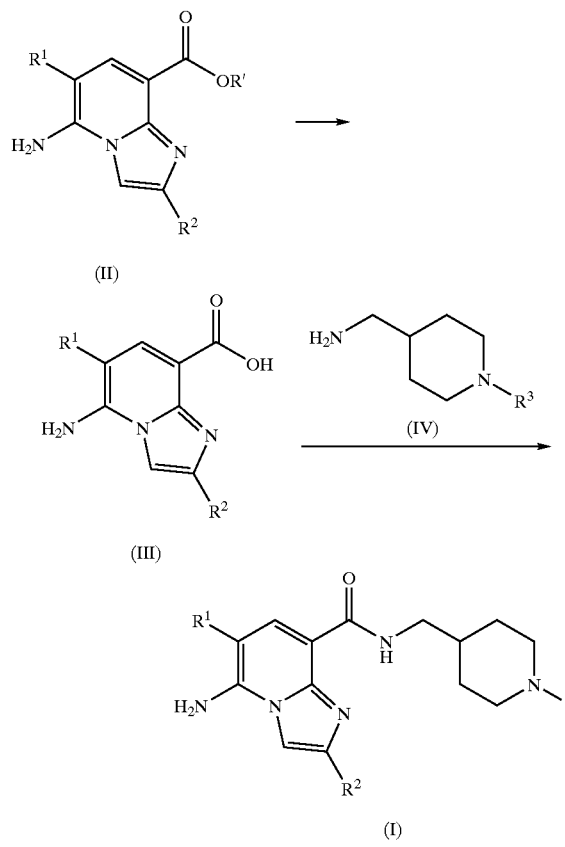

wherein R' is $C_{1-3}$ alkyl or benzyl.

In Scheme 1, the carboxylate compound (II) may be first subjected to saponification of the ester residue at the 8-position of the imidazopyridine ring, followed by acidification to afford a corresponding carboxylic acid (III). Then, the compound (III) may be coupled with the amine compound (IV) to give an imidazopyridine compound (I).

The saponification and the acidification may be carried out by conventional procedures. In a typical procedure, the saponification is carried out by treatment with sodium hydroxide or lithium hydroxide in a suitable reaction-inert solvent. Suitable solvents include, for example, alcohols such as methanol, ethanol, propanol, butanol, 2-methoxyethanol, and ethylene gylcol; ethers such as tetrahydrofuran (THF), 1,2-dimethoxyethane (DME), and 1,4-dioxane; halogenated hydrocarbons such as chloroform, dichloroethane, and 1,2-dichloroethane; amides such as N,N-dimethylformamide (DMF) and hexamethylphospholictriamide; and sulfoxides such as dimethyl sulfoxide (DMSO). This reaction may be carried out at a temperature in the range from −20 to 100° C., usually from 20° C. to 65° C. for 30 minutes to 24 hours, usually 60 minutes to 10 hour. In a typical procedure, the acidification is carried out by treatment with diluted hydrochloric acid or 10% aqueous citric acid in a suitable reaction-inert solvent such as water at a temperature in the range from −20 to 65° C., usually from 0° C. to 30° C. for 30 minute to 10 hour, usually 30 minutes to 2 hours.

The coupling reaction may be carried out in the presence of a suitable condensation agent in a reaction-inert solvent. Suitable condensation agents include 1,1'-carbonyldiimidazole (CDI), diisopropylcarbodiimide (DIC), dicyclohexylcarbodiimide (DCC), water soluble carbodiimide (WSC), 2-ethoxy-N-ethoxycarbonyl-1,2-dihydroquinoline, benzotriazol-1-yloxy-tris (dimethylamino) phosphonium hexafluorophosphate (BOP), diethyl azodicarboxylate-triphenylphosphine, diethylcyanophosphonate (DEPC), diphenylphosphorylazide (DPPA), bromotripyrrolidino phosphonium hexafluorophosphate (PyBrop[trademark]), bis(2-oxo-3-oxazolidinyl) phosphinic chloride (BOPCl), benzotriazole-1-yl-oxy-tris-pyrrolidino-phosphonium hexafluorophosphate (PyBOP), 2-(1-H-benzotriazole-1-yl)-1,1,3,3,-tetramethyluronium hexafluorophosphate (HBTU) and ethyl chloroformate. Suitable reaction-inert solvents include aqueous or non-aqueous organic solvents such as THF, DMF, 1,4-dioxane, acetone, DME and acetonitrile; and halogenated hydrocarbons such as chloroform, dichloromethane and 1,2-dichloroethane (preferably dichloromethane). This reaction may be carried out at a temperature in the range from −20 to 80° C., usually from 0° C. to 30° C. for 30 minutes to 100 hours, usually 5 hours to 24 hours.

Scheme 2:

The carboxylate compounds (II) used as starting materials in Scheme 1 may be prepared in the following reaction steps.

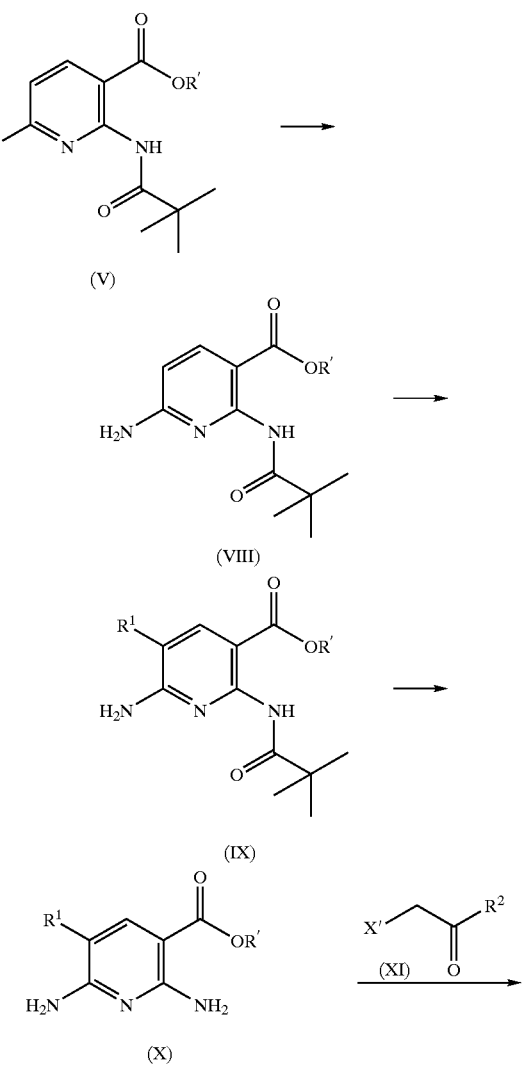

-continued

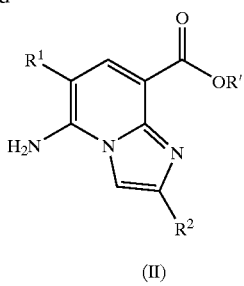

(II)

+

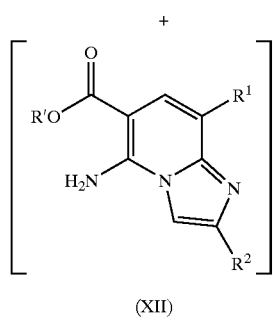

(XII)

In Scheme 2, a nicotinate compound (V) wherein R' is $C_{1-3}$ alkyl or benzyl and Z is halogen; and the amino group is protected by a pivaloyl group, may be reacted with an ammonia to obtain a compound (VIII). This reaction is generally carried out in a sealed tube. This reaction can be carried out in a suitable reaction-inert solvent such as methanol, ethanol, propanol, butanol, 2-methoxyethanol and THF. This reaction may be carried out at a temperature in the range from 30 to 150° C., usually from 50° C. to 100° C. for 30 minutes to 24 hours, usually 30 minutes to 12 hours. When $R^1$ is halo, the compound (VIII) is treated with halogen or N-halogenated succimide or SELECTFLUOR™ (1-(chloromethyl)-4-fluoro-1,4-diazoniabicyclo[2.2.2]octane ditetrafluoroborate commercially available from Aldrich) under appropriate conditions, to obtain a compound (IX) wherein $R^1$ is halo. This reaction can be carried out in a suitable reaction-inert solvent such as carboxylic acids (e.g., acetic acid, propionic acid and butylic acid); halogenated hydrocarbons such as chloroform, dichloroethane and 1,2-dichloroethane; amides such as DMF and hexamethylphospholictriamide; sulfoxides such as DMSO; acetonitrile; benzene, toluene, xylene; and pyridine. This reaction may be carried out at a temperature in the range from 0 to 80° C., usually from 25 to 70° C. for 5 minutes to 24 hours, usually 15 minutes to 8 hours. Then, the compound (IX) may be subject to deprotection of an amino-protecting group, to obtain a compound (X). The deprotection may be carried out in the presence of base (e.g., potassium tert-butoxide, sodium ethoxide and sodium hydroxide) or acids (e.g., hydrochloric acid and sulfuric acid). The deprotection can be carried out in a suitable reaction-inert solvent such as methanol at a temperature in the range from 25 to 80° C., usually from 50 to 65° C. for 10 minutes to 24 hours, usually 30 minutes to 10 hours.

Then, the compound (X) may be reacted with a compound (XI) wherein X' is halogen, to obtain a compound (II) and a compound (XII). This reaction can be carried out in the presence of 2-halogenated aldehyde or 2-halogenated ketone (compound (IX)) in a suitable reaction-inert solvent such as methanol, ethanol, propanol and butanol at a temperature in the range from 25 to 120° C., usually from 50° C. to 65° C. for 8 hours to 72 hours, usually 8 hours to 24 hours. The resulting mixture of the compound (II) and the compound (XII) may be subjected to conventional separation techniques to obtain the compound (II). Suitable conventional separation techniques include silica gel column chromatography.

In addition, starting compounds of formula (V) are known or may be prepared from a known compound according to procedures known to those skilled in the art.

Scheme 3:

Compounds (I') (Compound (I) wherein $R^1$ is hydrogen) can be prepared by subjecting a compound (I) wherein $R^1$ is halo, to catalytic hydrogenation.

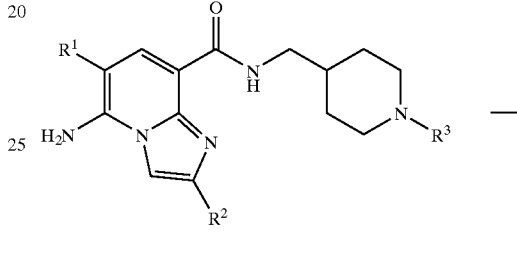

(I)

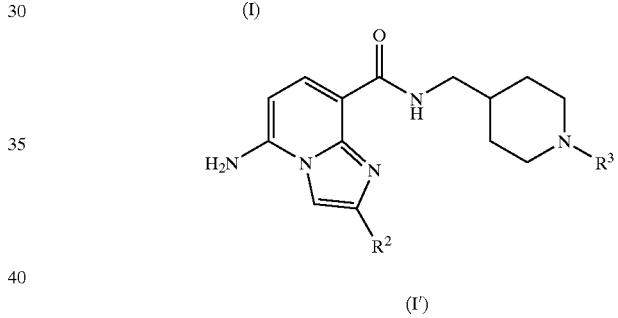

(I')

In Scheme 3, the catalytic hydrogenation can be carried out in the presence of hydrogen or hydrogen source such as ammonium formate, triethylsilane and a suitable metal containing catalysts such as palladium, platinum, nickel, platinum oxide and rhodium in a suitable reaction-inert solvent such as methanol. The preferred catalyst is palladium on carbon. This hydrogenation can be carried out at a temperature in the range from 20 to 100° C., usually from 25° C. to 80° C. for 5 minutes to 48 hours, usually 30 minutes to 2 hours.

Scheme 4:

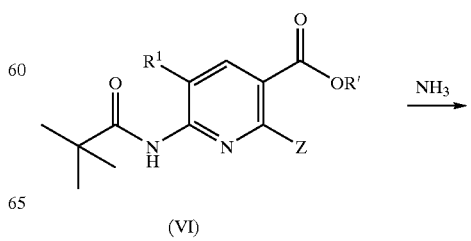

(VI)

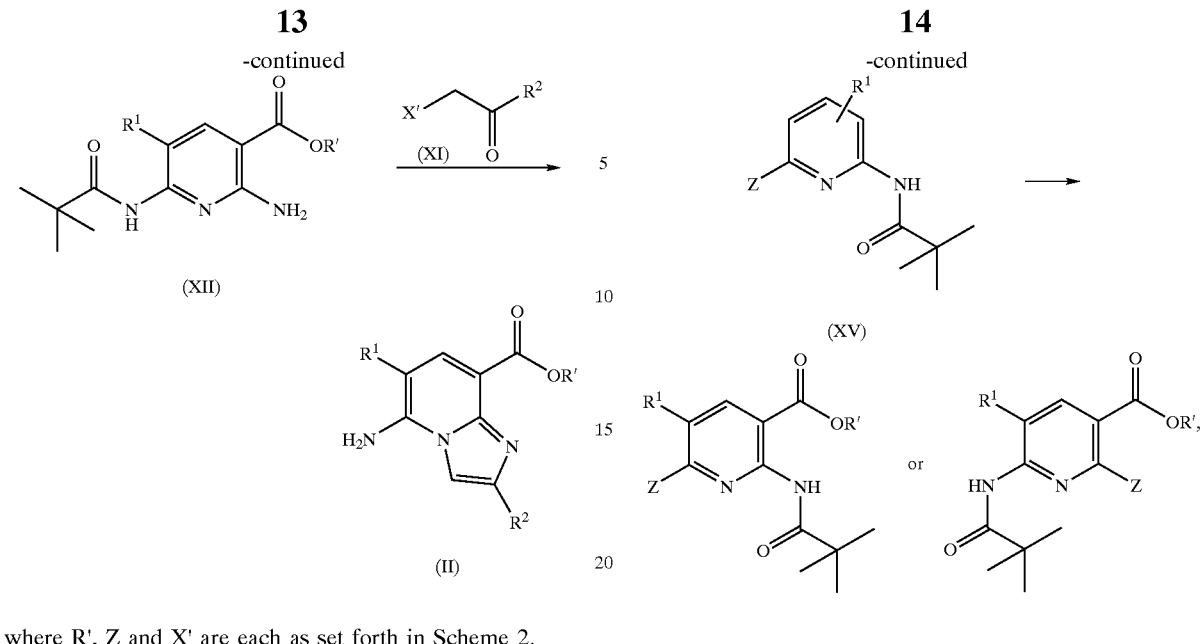

where R', Z and X' are each as set forth in Scheme 2.

In scheme 4, the compound (VI) may be reacted with an ammonia water to obtain a compound (VII). This reaction is generally carried out in a sealed tube. This reaction can be carried out in a suitable reaction-inert solvent. Suitable solvents include, for example, alcohols such as methanol, ethanol, propanol, butanol, 2-methoxyethanol and ethlene gylcol; ethers such as THF, DME, diethyl ether, diisopropyl ether, diphenyl ether and 1,4-dioxane; halogenated hydrocarbons such as chloroform, dichloroethane and 1,2-dichloroethane; amides such as DMF and hexamethylphospholictriamide; sulfoxides such as DMSO; acetonitrile; benzene, toluene, xylene; and pyridine. This reaction may be carried out at a temperature in the range from 30 to 150° C., usually from 50° C. to 100° C. for 30 minutes to 24 hours, usually 30 minutes to 12 hours. Compounds (II) may be prepared by reacting a compound (VII) with the compound (XI) under appropriate conditions. This reaction can be carried out in a suitable reaction-inert solvent such as methanol. This reaction may be carried out at a temperature in the range from 25 to 65° C., usually from 50° C. to 65° C. for 30 minutes to 48 hours, usually 30 minutes to 12 hours.

Scheme 5:

The nicotinate compounds (V') and (VI) used as starting materials in Scheme 2, 4 and 6 may be prepared in the following reaction steps.

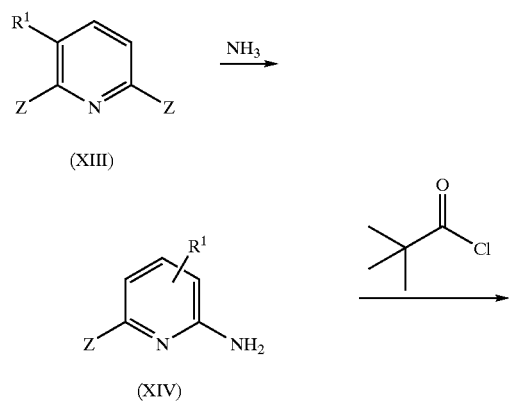

where R' is as set forth in Scheme 2.

In scheme 5, a pyridine compound (XIII) wherein Z, each of which can be the same or different, is halogen, may be reacted with an ammonia water to obtain a compound (XIV). This reaction is generally carried out in a sealed tube. This reaction may be carried out at a temperature in the range from 50 to 200° C., usually from 100° C. to 160° C. for 30 minutes to 24 hours, usually 30 minutes to 12 hours. The compound (XIV) is treated with acyl chloride, for example, pivaloyl chloride in the presence of base, such as diisopropylethylamine, triethylamine, pyridine and lutidine to obtain a mixture of compound (XV). This reaction can be carried out in a suitable reaction-inert solvent. Suitable solvents include, for example, halogenated hydrocarbons such as chloroform, dichloroethane and 1,2-dichloroethane. This reaction may be carried out at a temperature in the range from −20 to 50° C., usually from −10° C. to 30° C. for 30 minutes to 24 hours, usually 30 minutes to 10 hours. The compound (XV) is treated with alkaline methal, for example, n-BuLi followed by alkyl haloformate, for example, ethyl chloroformate or carbobenzyloxychloride to obtain a compound (V') and (VI). This reaction can be carried out in a suitable reaction-inert solvent. Suitable solvents include, for example, ethers such as THF, DME, diethyl ether, diisopropyl ether, diphenyl ether and 1,4-dioxane. This reaction may be carried out at a temperature in the range from −100 to 50° C., usually from −100 to 20° C. for 5 minutes to 24 hours, usually 15 minutes to 8 hours. In addition, starting compounds of formula (XIII) are known or may be prepared from a known compound according to procedures known to those skilled in the art, for example, Helv. Chim. Acta (1976), 59, 229–35, J. Chem. Soc., Perkin Trans. 1 (1996), 519–24 and J. Chem. Soc., Chem. Commun. (1988), 1482–3.

Scheme 6:

The carboxylate compounds (II) used as starting materials in Scheme 1 may be prepared in the following reaction steps.

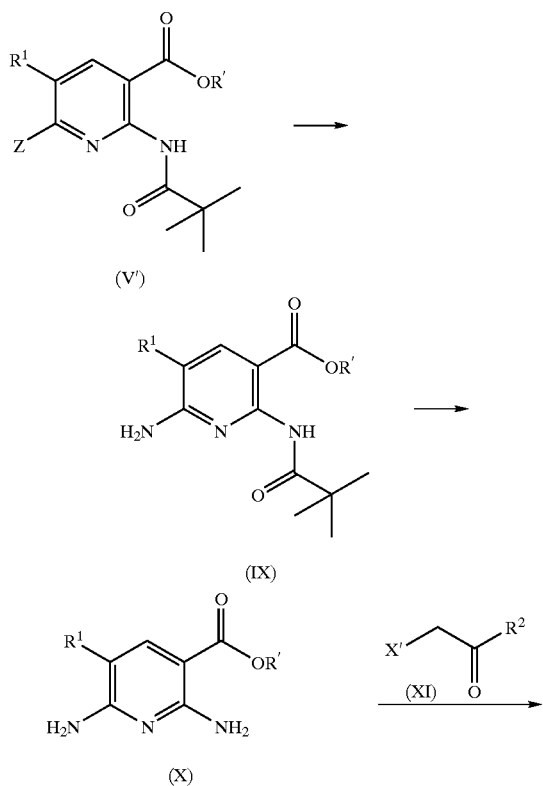

an amino-protecting group, to obtain a compound (X). The deprotection may be carried out in the presence of base (e.g., potassium tert-butoxide, sodium ethoxide and sodium hydroxide) or acids (e.g., hydrochloric acid and sulfuric acid). The deprotection can be carried out in a suitable reaction-inert solvent such as methanol at a temperature in the range from 25 to 80° C., usually from 50 to 65° C. for 10 minutes to 24 hours, usually 30 minutes to 10 hours.

Then, the compound (X) may be reacted with a compound (XI) where X' is halogen to obtain a compound (II) and a compound (XII). This reaction can be carried out in the presence of 2-halogenated aldehyde or 2-halogenated ketone (compound (XI)) in a suitable reaction-inert solvent such as methanol, ethanol, propanol and butanol at a temperature in the range from 25 to 120° C., usually from 50° C. to 65° C. for 8 hours to 72 hours, usually 8 hours to 24 hours. The resulting mixture of the compound (II) and the compound (XII) may be subjected to conventional separation techniques to obtain the compound (II). Suitable conventional separation techniques include silica gel column chromatography.

Scheme 7:

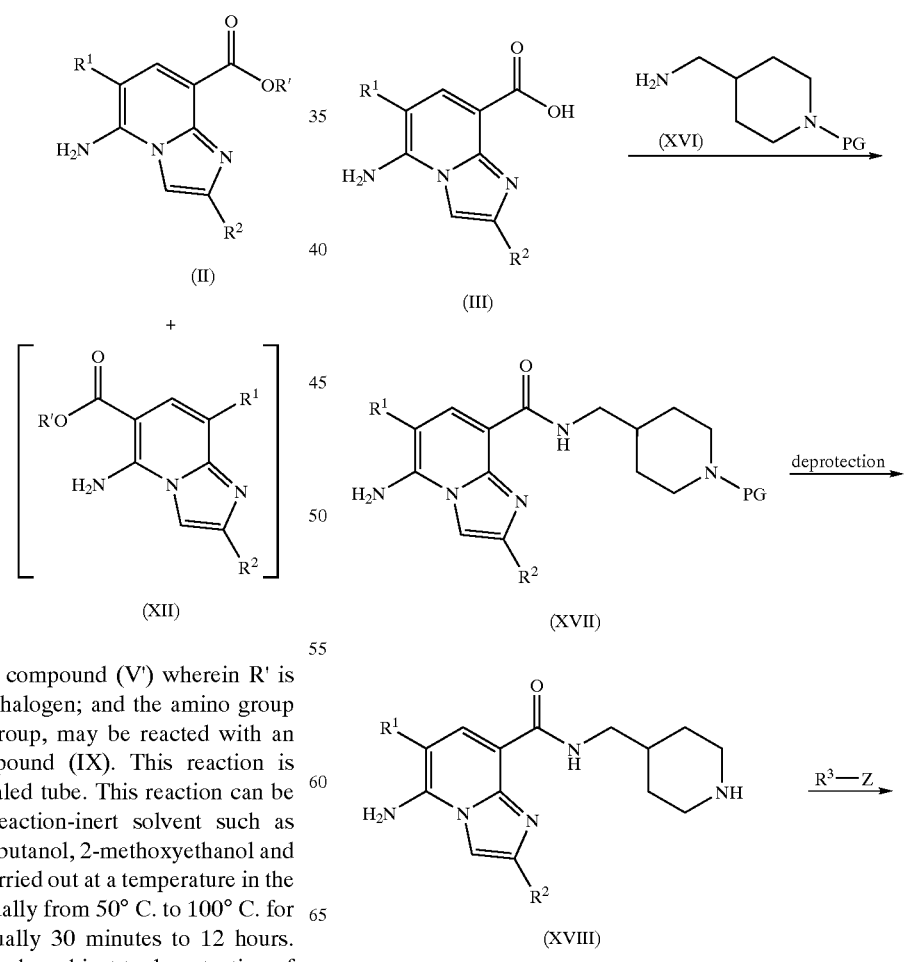

In Scheme 6, a nicotinate compound (V') wherein R' is $C_{1-3}$ alkyl or bezyl and Z is halogen; and the amino group is protected by a pivaloyl group, may be reacted with an ammonia to obtain a compound (IX). This reaction is generally carried out in a sealed tube. This reaction can be carried out in a suitable reaction-inert solvent such as methanol, ethanol, propanol, butanol, 2-methoxyethanol and THF. This reaction may be carried out at a temperature in the range from 30 to 150° C., usually from 50° C. to 100° C. for 30 minutes to 24 hours, usually 30 minutes to 12 hours. Then, the compound (IX) may be subject to deprotection of

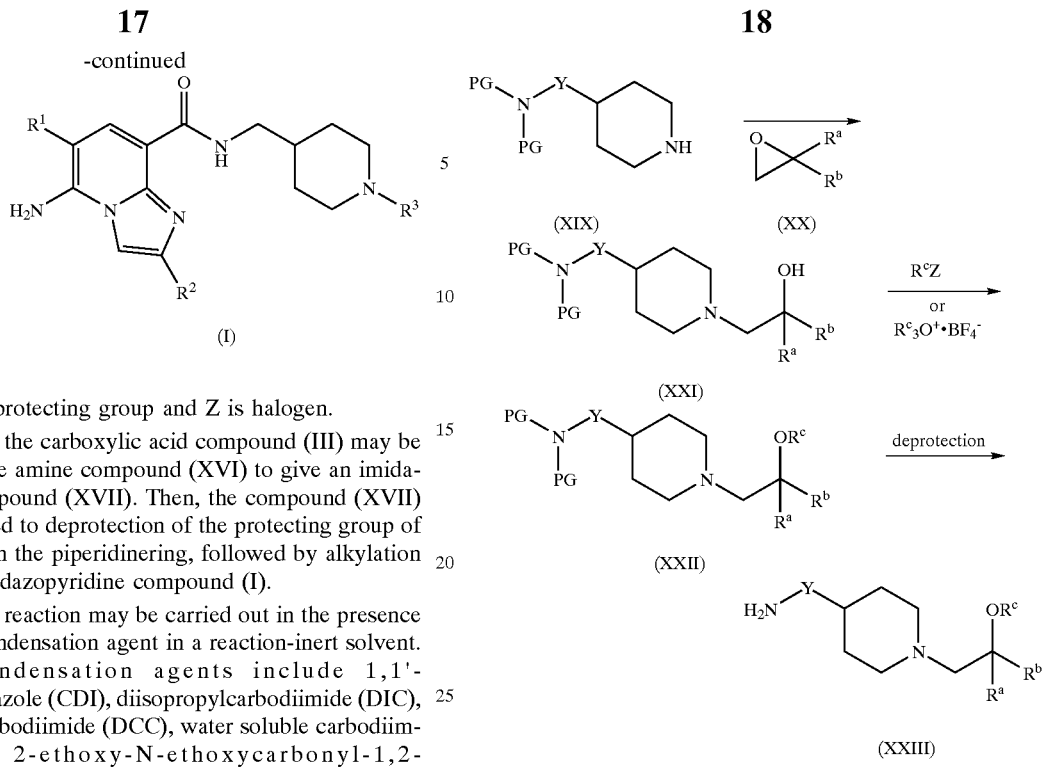

where PG is a protecting group and Z is halogen.

In Scheme 7, the carboxylic acid compound (III) may be coupled with the amine compound (XVI) to give an imidazopyridine compound (XVII). Then, the compound (XVII) may be subjected to deprotection of the protecting group of nitrogen atom in the piperidinering, followed by alkylation to afford an imidazopyridine compound (I).

The coupling reaction may be carried out in the presence of a suitable condensation agent in a reaction-inert solvent. Suitable condensation agents include 1,1'-carbonyldiimidazole (CDI), diisopropylcarbodiimide (DIC), dicyclohexylcarbodiimide (DCC), water soluble carbodiimide (WSC), 2-ethoxy-N-ethoxycarbonyl-1,2-dihydroquinoline, benzotriazol-1-yloxy-tris(dimethylamino)phosphonium hexafluorophosphate (BOP), diethyl azodicarboxylate-triphenylphosphine, diethylcyanophosphonate (DEPC), diphenylphosphorylazide (DPPA), bromotripyrrolidino phosphonium hexafluorophosphate (PyBrop[trademark]), bis(2-oxo-3-oxazolidinyl)phosphinic chloride (BOPCl), benzotriazole-1-yl-oxy-tris-pyrrolidino-phosphonium hexafluorophosphate (PyBOP), 2-(1-H-benzotriazole-1-yl)-1,1,3,3,-tetramethyluronium hexafluorophosphate (HBTU) and ethyl chloroformate. Suitable reaction-inert solvents include aqueous or non-aqueous organic solvents such as THF, DMF, 1,4-dioxane, acetone, DME and acetonitrile; and halogenated hydrocarbons such as chloroform, dichloromethane and 1,2-dichloroethane (preferably dichloromethane). This reaction may be carried out at a temperature in the range from −20 to 80° C., usually from 0° C. to 30° C. for 30 minutes to 100 hours, usually 5 hours to 24 hours.

The obtained amino compound may be subjected to deprotection of an amino-protecting group, to obtain a compound (XVIII). The deprotection may be carried out by a number of standard procedures known to those skilled in the art (e.g., "Protection for the Hydroxy Group and the Amino Group", in *Protective Groups in Organic Synthesis*, 2nd Edition, T. W. Greene and P. G. M. Wuts, Ed., John Wiley and Sons, Inc. 1991, pp. 10–142, 309–405). Then, alkylation of amino group in piperidine ring may be carried out under the conventional conditions. The compound may be treated with appropriate alkyl halides ($R^6$-Z) in the presence of a base such as diisopropylethylamine, triethylamine, pyridine, lutidine, potassium carbonate, sodium bicarbonate, sodium carbonate or the like, in a reaction inert solvent such as dichrolomethane, THF or DMF at about 0° C. to about 100°° C. for about 5 minutes to about 48 hours.

Scheme 8:

An amino compound (XXIII) wherein $R^a$ and $R^b$ are $C_{1-4}$ alkyl and $R^c$ is $C_{1-6}$ alkyl, may be prepared in the following reaction steps.

where PG is a protecting group and Y is methylene.

In scheme 8, piperidine compound (XIX) may be reacted with an epoxide compound (XX) to obtain a hydroxy compound (XXI). This reaction can be carried out in a suitable reaction-inert solvent such as THF, DMF, acetonitrile, dichloromethane, 1,2-dichloroethane, DMSO, methylethylketone, methanol, ethanol, propanol, butanol, iso-butanol, sec-butanol and tert-butanol at a temperature in the range from −50 to 250° C., usually from 0° C. to 200° C. for 30 minutes to 100 hours, usually 1 hour to 80 hours. This reaction may be carried out in the presense of a methal halide such as sodium iodide, potassium iodide and lithium iodide. The conversion of hydroxy compound (XXI) to an alkoxy compound (XXII) may be carried out under the conventional method. The alkylation of a hydroxy group may be carried out under the conventional conditions. The compound may be treated with appropriate alkyl halides ($R^6$-Z) in the presence of a base such as sodium methoxide, sodium ethoxide, potassium tert-butoxide, sodium hydride or potassium hydride, or the like, in a reaction inert solvent such as diethyl ether, DME, DMSO, THF or DMF at about 0° C. to about 200° C., usually from 0° C. to 200° C., for about 5 minutes to about 100 hours, usually 1 hour to 80 hours. Alternatively, hydroxy compound (XXI) may be treated with $R^c_3O^+BF_4^{-31}$ to provide the compound (XXII). This reaction can be carried out in a suitable reaction-inert solvent such as dichloromethane, 1,2-dichloroethane, benzene, toluene and nitromethane at a temperature in the range from −50 to 200° C., usually from 0° C. to 100° C. for 30 minutes to 100 hours, usually 1 hour to 80 hours. The obtained compound (XXII) may be subjected to deprotection of an amino-protecting group, to obtain a compound (XXIII). The deprotection may be carried out by a number of standard procedures known to those skilled in the art (e.g., "Protection for the Hydroxy Group and the Amino Group", in *Protective Groups in Organic Synthesis*, 2nd Edition, T. W. Greene and P. G. M. Wuts, Ed., John Wiley and Sons, Inc. 1991, pp. 10–142, 309–405).

Scheme 9:

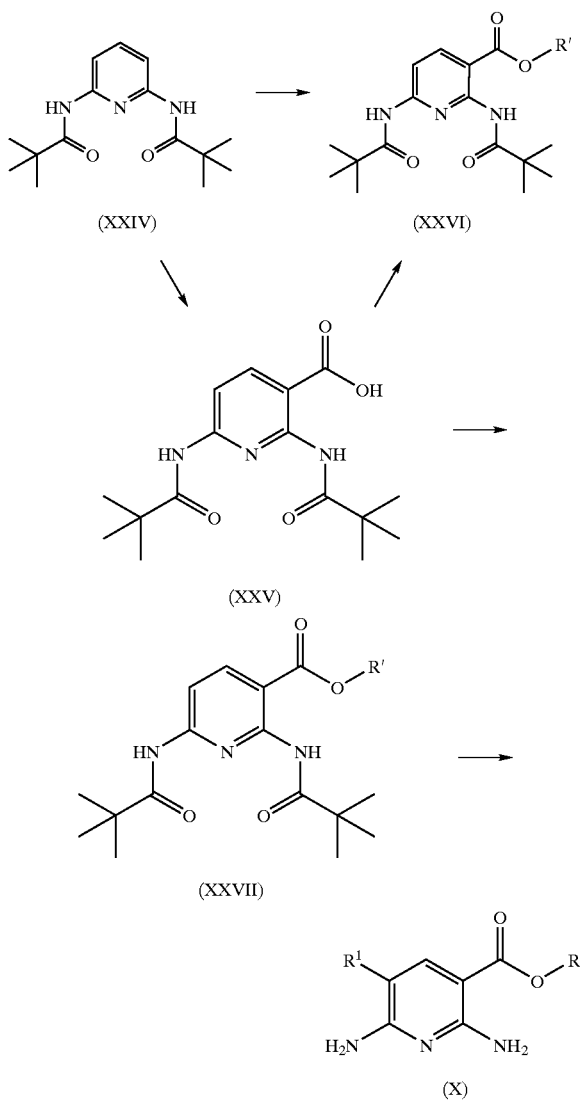

The nicotinate compounds (X) may be prepared in the following reaction steps.

In scheme 9, a pyridine compound (XXIV) may be treated with n-BuLi followed by R'COZ or R'COR' wherein R' is $C_{1-3}$ alkyl or benzyl and Z is halogen, to obtain a compound (XXVI). This reaction can be carried out in a suitable reaction-inert solvent. Suitable solvents include, for example, ethers such as THF, DME, diethyl ether, diisopropyl ether, diphenyl ether and 1,4-dioxane. This reaction may be carried out at a temperature in the range from −100 to 50° C., usually from −100 to 20° C. for 5 minutes to 24 hours, usually 15 minutes to 8 hours. Alternatively, the compound (XXVI) may be prepared from the pyridine compound (XXIV) by carboxylation followed by esterification. The pyridine compound (XXIV) may be treated with n-BuLi followed by carbondioxide (gas or dry ice) to obtain a carboxylic acid compound (XXV). This reaction can be carried out in a suitable reaction-inert solvent. Suitable solvents include, for example, ethers such as THF, DME, diethyl ether, diisopropyl ether, diphenyl ether and 1,4-dioxane. This reaction may be carried out at a temperature in the range from −100 to 50° C., usually from −100 to 20° C. for 5 minutes to 24 hours, usually 15 minutes to 8 hours. The compound (XXV) may be subjected to esterification to obtain the compound (XXVI). The esterification may be carried out by a number of standard procedures known to those skilled in the art (e.g., *Protective Groups in Organic Synthesis*, Third eddition. ed. T. W. Green and P. G. M. Wuts, Wiley-Interscience., pp 373–377.). Typical esterificaion can be carried out with a suitable $C_{1-3}$ alkylhalide or benzylhalide in the presense of a base in a suitable reaction-inert solvent. Suitable solvents include, for example, ethers such as THF, DME, diethyl ether, diisopropyl ether, diphenyl ether, DMF, DMSO, R'OH and 1,4-dioxane. Suitable bases include, for example, $K_2CO_3$, $Cs_2CO3$, $NaHCO_3$ and DBU. This reaction may be carried out at a temperature in the range from −100 to 200° C., usually from −10 to 100° C. for 1 to 72 hours, usually 2 to 60 hours. The esterification also carried out with trimethylsilyldiazomethane in a suitable reaction-inert solvent. Suitable solvents include, for example, methanol, benzene and toluene. This reaction may be carried out at a temperature in the range from −100 to 200° C., usually from −10 to 100° C. for 1 minute to 72 hours, usually 0.5 to 60 hours. The esterification also carried out with diazomethane in a suitable reaction-inert solvent. Suitable solvents include, for example, diethyl ether. This reaction may be carried out at a temperature in the range from −100 to 200° C., usually from −50 to 100° C. for 1 minute to 72 hours, usually 0.5 to 60 hours. Alternatively, the esterification may be carried out with R'OH, in the presense of a coupling agent and a tertiaryamine in a suitable solvent. Suitable coupling agents include, for example, DCC, WSC, diisoproopylcyanophosphonate (DIPC), BOPCl and 2,4,6-trichlorobenzoic acid chloride. Suitable tertiaryamines include, for example, diisoprpylethylamine, triethylamine. Suitable solvents include, for example, DMF, THF, diethyl ether, DME, dichloromethane and 1,2-dichloroethane. This reaction may be carried out at a temperature in the range from −100 to 200° C., usually from −50 to 100° C. for 1 minute to 100 hours, usually 0.5 to 80 hours. When $R^1$ is halo, the compound (XXVI) can be treated with halogen or N-halogenated succimide or SELECTFLUOR™ (1-(chloromethyl)-4-fluoro-1,4-diazoniabicyclo[2.2.2]octane ditetrafluoroborate commercially available from Aldrich) under appropriate conditions, to obtain a compound (XXVII) wherein $R^1$ is halo. This reaction can be carried out in a suitable reaction-inert solvent such as carboxylic acids (e.g., acetic acid, propionic acid and butylic acid); halogenated hydrocarbons such as chloroform, dichloroethane and 1,2-dichloroethane; amides such as DMF and hexamethylphospholictriamide; sulfoxides such as DMSO; acetonitrile; benzene, toluene, xylene; and pyridine. This reaction may be carried out at a temperature in the range from 0 to 80° C., usually from 25 to 70° C. for 5 minutes to 24 hours, usually 15 minutes to 8 hours. Then, the compound (XXVII) may be subject to deprotection of an amino-protecting group, to obtain a compound (X). The deprotection may be carried out in the presence of base (e.g., potassium tert-butoxide, sodium ethoxide and sodium hydroxide) or acids (e.g., hydrochloric acid and sulfuric acid). The deprotection can be carried out in a suitable reaction-inert solvent such as methanol at a temperature in the range from 25 to 80° C., usually from 50 to 65° C. for 10 minutes to 24 hours, usually 30 minutes to 10 hours.

In addition, starting compound of formula (XXIV) is known or may be prepared from a known compound according to procedures known to those skilled in the art, for example, *J. Am. Chem. Soc.* (1986), 108(12), 3310–18.

Scheme 10:

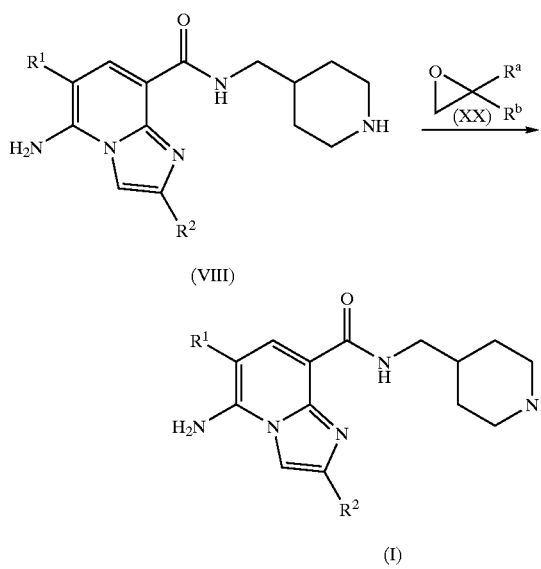

(VIII)

(I)

In scheme 10, the compound (XVIII) may be reacted with an epoxide compound (XX) to obtain the compound (I). This reaction can be carried out in a suitable reaction-inert solvent such as THF, DMF, acetonitrile, dichloromethane, 1,2-dichloroethane, DMSO, methylethylketone, methanol, ethanol, propanol, butanol, iso-butanol, sec-butanol and tert-butanol at a temperature in the range from −50 to 250° C., usually from 0° C. to 200° C. for 30 minutes to 100 hours, usually 1 hour to 80 hours. This reaction may be carried out in the presense of a methal halide such a as sodium iodide, potassium iodide and lithium iodide.

The present invention includes salt forms of the compounds (I) as obtained above. The present invention also provides salt forms of amides and esters of compound (I). Insofar as the imidazopyridine compounds of this invention are basic compounds, they are capable of forming a wide variety of different salts with various inorganic or organic acids.

The acids which are used to prepare the pharmaceutically acceptable acid addition salts of the aforementioned imidazopyridine base compounds of formula (I) are those which form non-toxic acid addition salts, i.e., salts containing pharmaceutically acceptable anions, such as the chloride, bromide, iodide, nitrate, sulfate or bisulfate, phosphate or acid phosphate, acetate, lactate, citrate or acid citrate, tartrate or bi-tartrate, succinate, malate, lumarate, gluconate, saccharate, benzoate, methanesulfonate, ethanesulfonate, benzenesulfonate, p-toluenesulfonate and pamoate (i.e., 1.1'-methylene-bis-(2-hydroxy-3-naphthoate). The acid addition salts can be prepared by conventional procedures.

The compounds of formula (I) of this invention may contain one or more asymmetric centers. Thus, the compounds can exist in separated (+)- and (−)-optically active forms, as well as in the racemic form thereof. The present invention includes all such forms within its scope. Individual isomers can be obtained by known methods, such as optically selective reaction or chromatographic separation in the preparation of the final product or its intermediate.

In addition, when the compounds of this invention form hydrates or solvates they are also within the scope of this invention.

The imidazopyridine compounds of this invention have 5-HT$_4$ receptor binding activity (e.g., agonist or antagonist activities), and thus are useful for the treatment or prevention of gastroesophageal reflux disease, gastrointestinal disease, gastric motility disorder, upper gut motility disorder, non-ulcer dyspepsia, functional dyspepsia, irritable bowel syndrome, constipation, dyspepsia, esophagitis, gastroesophageral disease, nausea, central nervous system disease, alzheimers disease, cognitive disorder, emesis, migraine, neurological disease, pain, ischaemic stroke, anxiety, cardiovascular disorders such as cardiac failure and heart arryhthmia, or the like in mammalian, especially human.

The compounds of the invention may advantageously be employed in combination with one or more other therapeutic ingredients selected from an antibiotic, anti-fungal and anti-viral agent.

Method for Assessing Biological Activities

The 5-HT$_4$ receptor binding affinity of the compounds of this invention are determined by the following procedures.

Membrane Preparation

Pig heads were supplied from an abattoir. Striatal tissues were dissected, weighed and homogenized in 15 volumes of 50 mM ice-cold HEPES (pH 7.5) in a Polytron homogenizer (30 sec at full speed). Suspension was centrifuged at 48,000 g and 4° C. for 15 min. The resulting pellet was resuspended in an appropriate volume of 50 mM ice-cold HEPES, dispensed into aliquots and stored at −80° C. until use.

Bovine heads were also supplied from an abattoir. Striatal tissues were dissected, weighed and homogenized in 20 volumes of 50 mM ice-cold Tris-HCl (pH 7.4) in a Polytron homogenizer (30 sec at full speed). Suspension was centrifuged at 20,000 g and 4° C. for 30 min. The resulting pellet was resuspended in 15 volumes of 50 mM ice-cold Tris-HCl, homogenized and centrifuged again in the same way. The final pellet was resuspended in an appropriate volume of 50 mM Tris-HCl, dispensed into aliquots and stored at −80° C. until use.

Cerebral cortical tissues were removed from male Sprague-Dawley (SD) rats (Japan SLC), weighed and placed in 10 volumes of 50 mM ice-cold Tris-HCl (pH 7.5). This was homogenized in a Polytron homogenizer (30 sec at full speed) and subsequently centrifuged at 48,000 g and 4° C. for 15 min. The resulting pellet was resuspended in 50 mM ice-cold Tris-HCl, homogenized and centrifuged again in the same way. The final pellet was resuspended in an appropriate volume of 50 mM Tris-HCl, dispensed into aliquots and stored at −80° C. until use.

The protein concentrations of homogenates were determined by Bradford method or BCA protein method (Pierce) with BSA as a standard.

Binding Assays

Affinity of compounds for pig or bovine 5-HT4 and rat 5-HT3 receptors were assessed with using radiolabeled specific ligands, GR 113808 ({1-[2-(methylsulfonyl)ethyl]-4-piperidinyl}[methyl-$^3$H]-1H-indole-3-carboxylate) and BRL 43694 (1-Methyl-N-(9-[methyl-$^3$H]-9-azabicyclo[3.3.1]non-3-yl)-1H-indazole-3-caboxamide). Compounds were incubated with 25–100 PM of [$^3$H]-GR 113808 (Amersham) and 0.6–1 mg protein of pig or bovine striatal membranes suspended in a final volume of 0.8–1 ml of 50 mM Tris-HCl (pH 7.5). Nonspecific binding was determined with 10–50 μM 5-HT. The binding of 0.3 nM [$^3$H]-BRL 43694 (NEN) was measured using 400 μg protein of rat cortical membranes suspended in a final volume of 500 μl of 50 mM Tris-HCl (pH 7.5). Nonspecific binding was determined with 10 μM 5-HT.

The plates were incubated at room temperature on a plate shaker for 30 min. The assays were stopped by rapid filtration using a Brandell cell harvester through Wallac-B filters pre-soaked in 0.2% poly(ethylenimine) at 4° C. for 60–90 min. The filters were washed three times with 1 ml of ice-cold 50 mM HEPES, and were dried in a microwave or at room temperature. They were bagged and heated with meltilex scintillant (Wallac) or soaked in BetaplateScint (Wallac). Receptor-bound radioactivity was quantified using Big-spot counter, Betaplate counter (Wallac) or LS counter (Packard).

Human 5-HT4 Binding

Human 5-HT$_{4(d)}$ transfected HEK293 cells were prepared and grown in-house. The collected cells were suspended in 50 mM HEPES (pH 7.4 at 4° C.) supplemented with protease inhibitor cocktail (Boehringer, 1:1000 dilution) and homogenized using a hand held Polytron PT 1200 disruptor set at full power for 30 sec on ice. The homogenates were centrifuged at 40,000×g at 4° C. for 30 min. The pellets were then resuspended in 50 mM HEPES (pH 7.4 at 4° C.) and centrifuged once more in the same manner. The final pellets were resuspended in an appropriate volume of 50 mM HEPES (pH 7.4 at 25° C.), homogenized, aliquoted and stored at −80° C. until use. An aliquot of membrane fractions was used for protein concentration determination using BCA protein assay kit (PIERCE) and ARVOsx plate reader (Wallac).

For the binding experiments, 25 μl of test compounds were incubated with 25 μl of [$^3$H]-GR113808 (Amersham, final 0.2 nM) and 150 μl of membrane homogenate and WGA-SPA beads (Amersham) suspension solutions (10 μg protein and 1 mg SPA beads/well) for 60 minutes at room temperature. Nonspecific binding was determined by 1 μM GR113808 (Tocris) at the final concentration. Incubation was terminated by centrifugation at 1000 rpm. Receptor-bound radioactivity was quantified by counting with Micro-Beta plate counter (Wallac).

All compounds prepared in the working examples as described below were tested by this method, and showed a Ki value of about 0.19 nM to about 47 nM with respect to the affinity to the 5-HT$_4$ receptor.

Functional Assay:

The presence of 5-HT$_4$ receptors in the rat oesophagus and the ability to demonstrate partial agonism in the TMM preparation are reported in the literature (See G. S. Baxter et al. Naunyn-Schmiedeberg's Arch Pharmacol (1991) 343: 439–446; M. Yukiko et al. JPET (1997) 283: 1000–1008; and J. J. Reeves et al. Br. J. Pharmacol. (1991) 103: 1067–1072). More specifically, partial agonist activity can be measured according to the following procedures.

Male SD rats (Charles River) weighing 250–350 g were stunned and then killed by cervical dislocation. The oesophagus was dissected from immediately proximal to the stomach (including piece of stomach to mark distal end) up to the level of the trachea and then placed in fresh Krebs' solution.

The outer skeletal muscle layer was removed in one go by peeling it away from the underlying smooth muscle layer using forceps (stomach to tracheal direction). The remaining inner tube of smooth muscle was known as the TMM. This was trimmed to 2 cm from the original 'stomach-end' and the rest discarded.

The TMMs were mounted as whole 'open' tubes in longitudinal orientation in 5 ml organ baths filled with warm (32° C.) aerated Krebs. Tissues were placed under an initial tension of 750 mg and allowed to equilibrate for 60 minutes. The tissues were re-tensioned twice at 15 minute intervals during the equilibration period. The pump flow rate was set to 2 ml/min during this time.

Following equilibration, the pump was switched off. The tissues were exposed to 1 μM carbachol and contracted and reached a steady contractile plateau within 15 minutes. Tissues were then subject to 1 μM 5-HT (this was to prime the tissues). The tissues relaxed in response to 5-HT fairly rapidly—within 1 minute. As soon as maximal relaxation has occurred and a measurement taken, the tissues were washed at maximum rate (66 ml/min) for at least 1 minute and until the original baseline (pre-carbachol and 5-HT) has returned (usually, the baseline drops below the original one following initial equilibration). The pump flow rate was reduced to 2 ml/min and the tissues left for 60 minutes.

A cumulative concentration-effect-curve (CEC) to 5-HT was constructed across the range 0.1 nM to 1 μM, in half-log unit increments (5-HT curve 1 for data analysis). Contact time between doses was 3 minutes or until plateau established. Tissues responded quicker as concentration of 5-HT in the bath increases. At the end of the curve, the tissues were washed (at maximum rate) as soon as possible to avoid desensitisation of receptors. Pump rate was reduced to 2 ml/min and the tissues left for 60 minutes.

A second CEC was carried out—either to 5-HT (for time control tissues), another 5-HT$_4$ agonist (standard) or a test compound (curve 2 for data analysis). Contact time varied for other 5-HT$_4$ agonists and test compounds and was tailored according to the tissues' individual responses to each particular agent. In tissues exposed to a test compound, a high concentration (1 μM) of a 5-HT$_4$ antagonist (SB 203,186: 1H-Indole-3-carboxylic acid, 2-(1-piperidinyl) ethyl ester, Tocris) was added to the bath following the last concentration of test compound. This was to see if any agonist-induced relaxation (if present) could be reversed. SB 203,186 reversed 5-HT induced relaxation, restoring the tissue's original degree of carbachol-induced tone.

Agonist activity of test compounds was confirmed by pre-incubating tissues with 100 nM standard 5HT$_4$ antagonist such as SB 203,186. SB 203,186 was added to the bath 5 minutes before the addition of carbachol prior to curve 2. Tissues must be 'paired' for data analysis i.e. the test compound in the absence of SB 203,186 in one tissue was compared with the test compound in the presence of SB 203,186 in a separate tissue. It was not possible to carry out a curve 3 i.e. 5-HT curve 1, followed by the test compound curve 2 (−SB 203,186), followed by the test compound curve 3 (+SB 203,186).

Agonist-Induced cAMP Elevation in Human 5-HT$_{4(d)}$ Transfected HEK293 Cells

Human 5-HT$_{4(d)}$ transfected HEK293 cells were established in-house. The cells were grown at 37° C. and 5% CO$_2$ in DMEM supplemented with 10% FCS, 20 mM HEPES (pH 7.4), 200 μg/ml hygromycin B (Gibco), 100 units/ml penicillin and 100 μg/ml streptomycin.

The cells were grown to 60–80% confluence. On the previous day before treatment with compounds dialyzed FCS (Gibco) was substituted for normal and the cells were incubated overnight.

Compounds were prepared in 96-well plates (12.5 μl/well). The cells were harvested with PBS/1 mM EDTA, centrifuged and washed with PBS. At the beginning of the assay, cell pellet was resuspended in DMEM supplemented with 20 mM HEPES, 10 μM pargyline (Sigma) and 1 mM 3-isobutyl-1-methylxanthine (Sigma) at the concentration of 1.6×10$^5$ cells/ml and left for 15 minutes at room temperature. The reaction was initiated by addition of the cells into plates (12.5 μl/well). After incubation for 15 minutes at room temperature, 1% Triton X-100 was added to stop the reaction (25 μl/well) and the plates were left for 30 minutes at room temperature. Homogenous time-resolved fluorescence-based cAMP (Schering) detection was made according to the manufacturer's instruction. ARVOsx multilabel counter (Wallac) was used to measure HTRF (excitation 320 nm, emission 665 nm/620 nm, delay time 50 μs, window time 400 μs).

Data was analyzed based on the ratio of fluorescence intensity of each well at 620 nm and 665 nm followed by cAMP quantification using cAMP standard curve. Enhancement of cAMP production elicited by each compound was normalized to the amount of cAMP produced by 1000 nM serotonin (Sigma).

Human Dofetilide Binding

Human HERG transfected HEK293S cells were prepared and grown in-house. The collected cells were suspended in 50 mM Tris-HCl (pH 7.4 at 4° C.) and homogenized using a hand held Polytron PT 1200 disruptor set at full power for 20 sec on ice. The homogenates were centrifuged at 48,000×g at 4° C. for 20 min. The pellets were then resuspended, homogenized, and centrifuged once more in the same manner. The final pellets were resuspended in an appropriate volume of 50 mM Tris-HCl, 10 mM KCl, 1 mM $MgCl_2$ (pH 7.4 at 4° C.), homogenized, aliquoted and stored at −80° C. until use. An aliquot of membrane fractions was used for protein concentration determination using BCA protein assay kit (PIERCE) and ARVOsx plate reader (Wallac).

Binding assays were conducted in a total volume of 200 μl in 96-well plates. Twenty μl of test compounds were incubated with 20 μl of [$^3$H]-dofetilide (Amersham, final 5 nM) and 160 μl of membrane homogenate (25 μg protein) for 60 minutes at room temperature. Nonspecific binding was determined by 10 μM dofetilide at the final concentration. Incubation was terminated by rapid vacuum filtration over 0.5% presoaked GF/B Betaplate filter using Skatron cell harvester with 50 mM Tris-HCl, 10 mM KCl, 1 mM $MgCl_2$, pH 7.4 at 4° C. The filters were dried, put into sample bags and filled with Betaplate Scint. Radioactivity bound to filter was counted with Wallac Betaplate counter.

$I_{HERG}$ Assay

HEK 293 cells which stably express the HERG potassium channel were used for electrophysiological study. The methodology for stable transfection of this channel in HEK cells can be found elsewhere (Z. Zhou et al., 1998, Biophysical journal, 74, pp230–241). Before the day of experimentation, the cells were harvested from culture flasks and plated onto glass coverslips in a standard MEM medium with 10% FCS. The plated cells were stored in an incubator at 37° C. maintained in an atmosphere of 95% $O_2$/5% $CO_2$. Cells were studied between 15–28 hrs after harvest.

HERG currents were studied using standard patch clamp techniques in the whole-cell mode. During the experiment the cells were superfused with a standard external solution of the following composition (mM); NaCl, 130; KCl, 4; $CaCl_2$, 2; $MgCl_2$, 1; Glucose, 10; HEPES, 5; pH 7.4 with NaOH. Whole-cell recordings was made using a patch clamp amplifier and patch pipettes which have a resistance of 1–3 MOhm when filled with the standard internal solution of the following composition (mM); KCl, 130; MGATP, 5; $MgCl_2$, 1.0; HEPES, 10; EGTA 5, pH 7.2 with KOH. Only those cells with access resistances below 15 MΩ and seal resistances >1 GΩ was accepted for further experimentation. Series resistance compensation was applied up to a maximum of 80%. No leak subtraction was done. However, acceptable access resistance depended on the size of the recorded currents and the level of series resistance compensation that can safely be used. Following the achievement of whole cell configuration and sufficient for cell dialysis with pipette solution (>5 min), a standard voltage protocol was applied to the cell to evoke membrane currents. The voltage protocol is as follows. The membrane was depolarized from a holding potential of −80 mV to +20 mV for 1000 ms. This was followed by a descending voltage ramp (rate 0.5 mV $msec^{-1}$) back to the holding potential. The voltage protocol was applied to a cell continuously throughout the experiment every 4 seconds (0.25 Hz). The amplitude of the peak current elicited around −40 mV during the ramp was measured. Once stable evoked current responses were obtained in the external solution, vehicle (0.5% DMSO in the standard external solution) was applied for 10–20 min by a peristalic pump. Provided there were minimal changes in the amplitude of the evoked current response in the vehicle control condition, the test compound of either 0.3, 1, 3, 10 μM was applied for a 10 min period. The 10 min period included the time which supplying solution was passing through the tube from solution reservoir to the recording chamber via the pump. Exposing time of cells to the compound solution was more than 5 min after the drug concentration in the chamber well reached the attempting concentration. There reversibility. Finally, the cells was exposed to high dose of dofetilide (5 μM), a specific IKr blocker, to evaluate the insensitive endogenous current.

All experiments were performed at room temperature (23±1° C.). Evoked membrane currents were recorded on-line on a computer, filtered at 500–1 KHz (Bessel −3 dB) and sampled at 1–2 KHz using the patch clamp amplifier and a specific data analysing software. Peak current amplitude, which occurred at around −40 mV, was measured off line on the computer.

The arithmetic mean of the ten values of amplitude was calculated under control conditions and in the presence of drug. Percent decrease of $I_N$ in each experiment was obtained by the normalized current value using the following formula: $I_N=(1-I_D/I_C)\times100$, where $I_D$ is the mean current value in the presence of drug and $I_C$ is the mean current value under control conditions. Separate experiments were performed for each drug concentration or time-matched control, and arithmetic mean in each experiment is defined as the result of the study.

The imidazopyridine compounds of this invention can be administered via either the oral, parenteral or topical routes to mammals. In general, these compounds are most desirably administered to humans in doses ranging from about 0.3 mg to about 750 mg per day, preferably from about 10 mg to about 500 mg per day, although variations will necessarily occur depending upon the weight and condition of the subject being treated, the disease state being treated and the particular route of administration chosen. However, for example, a dosage level that is in the range of from about 0.06 mg to about 2 mg per kg of body weight per day is most desirably employed for treatment of inflammation.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging from about 5% to about 70% by weight, preferably about 10% to about 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath temperature of up to 60° C.; reactions were monitored by thin layer chromatography (tlc) and reaction times are given for illustration only; melting points (m.p.) given are uncorrected (polymorphism may result in different melting points); the structure and purity of all isolated compounds were assured by at least one of the following techniques: tlc (Merck silica gel 60 $F_{254}$ precoated TLC plates or Merck $NH_2$ $F_{254s}$ precoated HPTLC plates), mass spectrometry, nuclear magnetic resonance (NMR), infrared red absorption spectra (1R) or microanalysis. Yields are given for illustrative purposes only. Flash column chromatography was carried out using Merck silica gel 60 (230–400 mesh ASTM) or Fuji Silysia Chromatorex® DU3050 (Amino Type, 30~50 μm). Low-resolution mass spectral data (EI) were obtained on a Automass 120 (JEOL) mass spectrometer. Low-resolution mass spectral data (ESI) were obtained on a Quattro II (Micromass) mass spectrometer. NMR data was determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br. =broad, etc. IR spectra were measured by a Shimazu infrared spectrometer (IR-470). Optical rotations were measured using a JASCO DIP-370 Digital Polarimeter (Japan Spectroscopic CO, Ltd.). Chemical symbols have their usual meanings; b.p. (boiling point), m.p. (melting point), 1 (liter(s)), ml (milliliter(s)), g (gram(s)), mg (milligram(s)), mol (moles), mmol (millimoles), eq. (equivalent(s)).

Example 1

5-amino-6-chloro-N-{[1-(3,3-dimethyl-2-oxobutyl) piperidin-4-yl]methyl}imidazo[1,2-a]pyridine-8-carboxamide

METHOD A:

Step 1. Ethyl 2-amino-6-[(2,2-dimethylpropanoyl)amino] nicotinate

To a stirred solution of ethyl 6-[(2,2-dimethylpropanoyl) amino]-2-fluoronicotinate (M. C. Coldwell et al., *Bioorg. Med. Chem. Lett.*, 1995, 39, 5, 1.5 g, 5.59 mmol) in 2-propanol (16 mL) was added 25% aqueous ammonia (4 mL) and the mixture was heated in a sealed tube at 70° C. for 4.5 h. After cooling to room temperature, water was added and the mixture was extracted with ethyl acetate. The separated organic layer was concentrated in vacuo and the residue was chromatographed on a column of silica gel eluting with ethyl acetate/pentane (1:6 to 1:2) to give 810 mg (55%) of the title compound as a white solid.

MS (TSP+) m/z: 266 (M+H).

$^1$H-NMR (CDCl$_3$) δ: 1.35 (9H, s), 1.36 (3H, t), 4.30 (2H, q), 7.54 (1H, d), 7.80 (1H, br s), 8.12 (1H, d). A signal due to NH$_2$ was not observed.

Step 2. Ethyl 2-amino-5-chloro-6-[(2,2-dimethylpropanoyl) amino]nicotinate

To a solution of ethyl 2-amino-6-[(2,2-dimethylpropanoyl)amino]nicotinate (Example 1, METHOD A, Step 1, 805 mg, 3.03 mmol) in acetic acid (15 ml) was added a solution of chlorine in acetic acid (0.89 M, 8.5 mL, 7.6 mmol), and the mixture was stirred at room temperature for 15 min. The solvent was removed in vacuo. The obtained residue was taken up in ethyl acetate (150 mL) and washed with saturated sodium bicarbonate, dried over magnesium sulfate, and evaporated in vacuo. The residue was chromatographed on a column of silica gel eluting with ethyl acetate/pentane (1:2) to give 685 mg (76%) of the title compound as a white crystal.

MS (TSP+) m/z: 300 (M+H).

$^1$H-NMR (CDCl$_3$) δ: 1.35 (9H, s), 1.38 (3H, t, J=7.1 Hz), 4.30 (2H, q, J=7.1 Hz), 8.09 (1H, s), 8.20 (1H, br s). A signal due to NH$_2$ was not observed.

Step 3. Ethyl 5-amino-6-chloroimidazo[1,2-a]pyridine-8-carboxylate

To a solution of ethyl 2-amino-5-chloro-6-[(2,2-dimethylpropanoyl)amino]nicotinate (Example 1, METHOD A, Step 2, 685 mg, 2.12 mmol) in ethanol (10 mL) was added 50% aqueous chloroacetaldehyde (430 μL, 3.4 mmol), and the mixture was refluxed with stirring overnight. The mixture was treated with charcoal and filtered. The filtrate was dry-loaded onto silica gel and chromatographed on a column of silica gel eluting with dichloromethane/methanol/25% aqueous ammonia (97:3:1 to 95:5:0.5) to give 220 mg (40%) of the title compound as a white solid.

MS (TSP+) m/z: 240 (M+H).

$^1$H-NMR (DMSO-d$_6$) δ: 1.29 (3H, t, J=7.1 Hz), 4.25 (2H, q, J=6.9 Hz), 7.60 (1H, s), 7.80 (2H,-br), 7.89 (1H, s), 8.09 (1H, s).

Step 4. 5-Amino-6-chloroimidazo[1,2-a]pyridine-8-carboxylic acid

To a stirred solution of ethyl 5-amino-6-chloroimidazo[1,2-a]pyridine-8-carboxylate (Example 1, METHOD A, Step 3, 217 mg, 0.91 mmol) in methanol (5 mL) was added 1N aqueous lithium hydroxide (500 μL) and the mixture was stirred overnight at room temperature. The solvent was removed in vacuo and acidified with 1N hydrochloric acid. The resultant precipitate was collected by filtration to give 165 mg (86%) of the title compound as a white solid.

MS (TSP+) m/z: 212 (M+H).

$^1$H-NMR (DMSO-d$_6$) δ: 8.00 (1H, s), 8.21 (1H, s), 8.57 (1H, s), 8.90 (2H, br s).

Step 5. 5-amino-6-chloro-N-{[1-(3,3-dimethyl-2-oxobutyl)piperidin-4-yl]methyl}imidazo[1,2-a]pyridine-8-carboxamide A mixture of 5-amino-6-chloroimidazo[1,2-a]pyridine-8-carboxylic acid (Example 1, METHOD A, Step 4, 250 mg, 1.2 mmol), 1-[4-[(aminomethyl)piperidin-1-yl]-3,3-dimethylbutan-2-one* (426 mg, 2.0 mmol), diethyl cyanophosphonate (305 μL, 2.0 mmol) and diisopropylethylamine (345 μL, 2.0 mmol) in N,N-dimethylformamide (5 mL) was stirred at 0° C. for 30 min and at room temperature for 22 h. After addition of water (10 mL), the mixture was extracted with ethyl acetate (10 mL×3) and washed with brine (10 mL). Removal of the solvent and purification by column chromatography on basic silica gel eluting with ethyl acetate/hexane (1:1) gave a solid (266 mg), which was washed with diethyl ether and hexane and collected by filtration to give 225 mg (0.56 mmol, 47%) of the title compound as a pale pink solid.

* Preparation of 1-[4-[(aminomethyl)piperidin-1-yl]-3,3-dimethylbutan-2-one

MS (ESI+) m/z: 406 (M+1).

IR (KBr) ν: 3454, 3304, 3263, 3153, 2932, 1717, 1634, 1609, 1553, 1516, 1491, 1331, 1265, 1232, 700 cm$^{-1}$.

$^1$H-NMR (CDCl$_3$) δ: 1.15 (9H, s), 1.45–1.82 (5H, m), 2.00–2.07 (2H, m), 2.90–2.94 (2H, m), 3.36 (2H, s), 3.44–3.48 (2H, m), 5.24–5.30 (2H, m), 7.48–7.50 (1H, m), 7.63 (1H, s), 8.22 (1H, s), 10.06 (1H, br).

Anal. Calcd. for C$_{20}$H$_{28}$ClN$_5$O$_2$.0.1H$_2$O: C, 58.92; H, 6.97; N, 17.18. Found: C, 58.55; H, 7.07; N, 16.88.

Step 1, benzyl [1-(3,3-dimethyl-2-oxobutyl)piperidin-4-yl]methylcarbamate

To a solution of benzyl piperidin-4-ylmethylcarbamate (*Tetrahedron Lett.* 1990, 31, 6903, 6.9 g, 27.8 mmol) in N,N-dimethylformamide (60 mL) were added triethylamine (9.7 mL, 69.5 mmol) and 1-bromo-3,3-dimethylbutan-2-one (7.9 g, 41.7 mmol) at room temperature. The mixture was stirred at room temperature for 2 h and quenched with water (60 mL) followed by extraction with ethyl acetate-toluene mixture (3×30 mL). Concentration and purification by column chromatography on silica gel eluting with ethyl acetate/hexane (2:1) gave the title compound (9.6 g, 100%) as a pale yellow solid.

MS (ESI+) m/z: 347 (M+1).

$^1$H-NMR (CDCl$_3$) δ: 1.15 (9H, s), 1.36–1.55 (3H, m), 1.64–1.68 (2H, m), 1.98–2.04 (2H, m), 2.88–2.92 (2H, m), 3.07–3.11 (2H, m), 3.37 (2H, s), 5.09 (2H, s), 7.31–7.36 (5H, m).

Step 2. 1-[4-(aminomethyl)piperidin-1-yl]-3,3-dimethylbutan-2-one

A mixture of benzyl [1-(3,3-dimethyl-2-oxobutyl)piperidin-4-yl]methylcarbamate (Step 1, 9.6 g, 27.7 mmol), 5% palladium on carbon (1.2 g) and acetic acid (4 mL) in ethanol (70 mL) was stirred at room temperature for 23 h under hydrogen atmosphere. Palladium on carbon was removed by filtration through a pad of Celite and the filtrate was concentrated. The residue was dissolved in ethyl acetate, washed with aqueous ammonia and extracted with ethyl acetate (5×50 mL). After dried over magnesium sulfate, removal of solvent gave the title compound (2.7 g, 46%) as a yellow oil.

MS (ESI+) m/z: 313 (M+1).

$^1$H-NMR (CDCl$_3$) δ: 1.15 (9H, s), 1.29–1.55 (3H, m), 1.68–1.71 (2H, m), 1.96–2.05 (2H, m), 2.57–2.59 (2H, m), 2.96–2.89 (2H, m), 3.37 (2H, s). A peak of NH$_2$ was not observed.

METHOD B: Preparation of methyl 5-amino-6-chloroimidazo[1,2-a]pyridine-8-carboxylate.

Step 1. Methyl 2,6-diamino-5-chloronicotinate.

A mixture of ethyl 2-amino-5-chloro-6-[(2,2-dimethylpropanol)amino]nicotinate (Example 1, METHOD A, Step 2, 300 mg, 1.0 mmol) and potassium tert-butoxide (337 mg, 3.0 mmol) in methanol (10 mL) was refluxed for 45 min. After evaporation of solvent, water (20 mL) was added. The mixture was extracted with ethyl acetate (10 mL×3), washed with brine (5 mL×3), dried over magnesium sulfate and evaporated. Drying in vacuo gave 177 mg (88%) of the title compound as a cream-white solid.

MS (EI) m/z: 202 (M$^+$).

$^1$H-NMR (DMSO-d$_6$) δ: 3.71 (3H, s), 6.77 (2H, br s), 6.94 (2H, br s), 7.72 (1H, s).

Step 2. Methyl 5-amino-6-chloroimidazo[1,2-a]pyridine-8-carboxylate

A mixture of methyl 2,6-diamino-5-chloronicotinate (Example 1, METHOD B, Step 1, 2.0 g, 9.92 mmol) and chloroacetaldehyde (1.2 mL, 10.91 mmol) in methanol (100 mL) was refluxed for 135 min. A further chloroacetaldehyde (1.2 mL, 10.91 mmol) was added and refluxing continued over 21 hours. The solvent was evaporated and the resulting solid co-evaporated with methanol (75 mL×2) prior to drying under vacuum, giving 2.62 g of crude material. The residue was chromatographed on a column of silica gel eluting with dichloromethane/methanol/25% aqueous ammonia (96.5:3.5:0.5 to 93:7:1) to give 1.52 g (68%) of the title compound as an off white powder.

MS (EI) m/z: 225 (M$^+$).

$^1$H-NMR (DMSO-d$_6$) δ: 3.35 (3H, s), 7.62 (1H, s), 7.85 (2H, br s), 7.92 (1H, s), 8.13 (1H, s).

Example 2

5-amino-6-chloro-n-{[1-(3,3-dimethyl-2-oxobutyl)piperidin-4-yl]methyl}-2-methylimidazo[1,2-a]pyridine-8-carboxamide Step 1. methyl 2,6-bis[(2,2-dimethylpropanoyl)amino]nicotinate In a 5 L, 4-necked round bottom flask, immersed in ice-cold ethanol-isopropanol (isopropanol 13%, −15° C.) bath, to a solution of 2,6-bis[(2,2-dimethylpropanoyl)amino]pyridine (*J. Am. Chem. Soc.* 1986, 108, 3310–3318, 126 g, 454 mmol) in anhydrous tetrahydrofuran (1.5 L) was added 2.66 M solution of n-buthyllithium in hexane (598 mL) dropwise from a dropping funnel (1 L) during the period of 6 h under nitrogen atmosphere (internal temperature was maintained at −15° C.~−5° C.). The resulting solution was stirred at 0° C. (internal temperature) for 12 h under nitrogen atmosphere. The formation of yellowish precipitate was noticed. Then the suspension was cooled to −15° C., dimethyl carbonate (194 mL, 2.3 mmol) was added in one portion. The reaction solution was stirred at 0° C. for 1 h, quenched with 1.5 L of 1 N aqueous hydrochloric acid, pH value was controlled to ~4.5 by adding 1 N aqueous hydrochloric acid, then 600 mL of ethyl acetate was added. After the layers were separated, the organic layer was washed with 1 L of 0.2 N aqueous NaOH (1 L) and brine (500 mL). Each aqueous layer was extracted with ethyl acetate (300 mL) twice. Combined organic layer was dried over sodium sulfate (~300 g) and concentrated. The residue was diluted with diisopropylether (300 mL) and the solution was evaoprated to remove the residual ethyl acetate azeotropically. The residue was dissolved with diisopropylether (360 mL) at 60° C. with gentle stirring, and then the small portion of the crystalline of the desired product (~5 mg) was added as seed. The formation of a pale yellow precipitate was noticed. The resulting suspension was cooled to room temperature (during the period of 2 h), and stirred at room temperature for 2 h. The suspension was filtered through paper filter, then the cake was washed with diisopropylether (80 mL). The solid was dried under reduced pressure at room temperature for 1 day to give the title compound (120 g, 358 mmol, 79%) as a pale yellow solid.

MS (EI) m/z: 335 (M$^+$)

$^1$H-NMR (CDCl$_3$) δ: 1.32 (9H, s), 1.35 (9H, s), 3.93 (3H, s), 8.04 (1H, d, J=8.8 Hz), 8.31 (1H, d, J=8.8 Hz), 9.32 (1H, br s), 11.47 (1H, br s).

Step 2. methyl 5-chloro-2,6-bis[(2,2-dimethylpropanoyl)amino]nicotinate

To a solution of methyl 2,6-bis[(2,2-dimethylpropanoyl)amino]nicotinate (Example 2, Step 1, 186 g, 555 mmol) in anhydrous N,N-dimethylformamide (930 mL) was added a solution of N-chlorosuccinimide (81.5 g, 610 mmol) in anhydrous N,N-dimethylformamide (560 mL) dropwise from a dropping funnel (1 L) during the period of 2.5 h at 70° C. (internal temperature) under nitrogen atmosphere. The resulting pale yellow solution was stirred at 70° C. for 2 h and allowed to cool to room temperature. The reaction solution was quenched with a solution of 250 g of ammonium chloride and 100 g of sodium hydrogen sulfite in 3 L of water and extracted with a mixture of ethyl acetate and hexane (3 L, 3:1). After the layers were separated, the organic layer was washed with water (2 L), dried over sodium sulfite (300 g) and evaporated. The residual pale yellow solid was added isopropylether (1.4 L) and the resulting mixture was stirred at 60° C. for 2 h. After the mixture was cooled to room temperature, the mixture was filtered through paper filter, and the cake was washed with isopropylether (200 mL), dried under reduced pressure at room temperature to give (153.9 g, 416 mmol) of the title compound as a white solid.

MS (ESI+) m/z: 370 (M+1)

$^1$H-NMR (CDCl$_3$) δ: 1.34 (18H, s), 3.94 (3H, s), 8.30 (1H, s), 8.51 (1H, br s), 11.12 (1H, brs).

Step 3. methyl 2,6-diamino-5-chloronicotinate

To a colorless solution of methyl 5-chloro-2,6-bis[(2,2-dimethylpropanoyl)amino]nicotinate (Example 2, Step 2, 153.9 g, 416 mmol) in methanol (1.5 L) was added a solution of potassium tert-butoxide (185 g, 1.65 mol) in methanol (500 mL) dropwise during the period of 20 min at room temperature under nitrogen atmosphere. Dissolving potassium tert-butoxide in methanol was exothermic, so potassium tert-butoxide must be added portionwise from powder addition funnel to methanol during the period of 2 h with ice-cold water bath. After the addition was completed, the reaction solution was stirred at reflux temperature for 1 h under nitrogen atmosphere, and cooled to room temperature. The resulting suspension was evaporated and ca. 1.3 L of methanol was removed (ca. 700 mL of methanol was remained). To this mixture was added water (1.2 L) and stirred at room temperature for 1 h with water bath (internal temperature was maintained at 20° C.), then the resulting suspension was filtered through paper filter and the pale yellow solid was dried under reduced pressure at 50° C. for 12 h to give 74.3 g (368.9 mmol, 89%) of the title compound as a pale yellow crystal.

Rf value: 0.28 (ethyl acetate/hexane=1:2).

$^1$H-NMR (DMSO-d$_6$) δ: 3.71 (3H, s), 6.77 (2H, br s), 6.94 (2H, br s), 7.72 (1H, s).

Step 4. methyl 5-amino-6-chloro-2-methylimidazo[1,2-a]pyridine-8-carboxylate

A mixture of methyl 2,6-diamino-5-chloronicotinate (Example 2, Step 3, 15 g, 74.4 mmol), bromoacetone (10.4 mL, 112 mmol) and sodium iodide (16.7 g, 112 mmol) in methanol (700 mL) was stirred under reflux for 22 h. Another 2.5 mL (33 mmol) of bromoacetone was added and the stirring was continued for 24 h. The reaction mixture was quenched with saturated aqueous sodium carbonate and removed methanol in vacuo. The residue was extracted with ethyl acetate (250 mL×10) adding a small amount of methanol to dissolve the organic solid. The organic extracts were dried over sodium sulfate and concentrated. Purification by column chromatography on silica gel eluting with dichloromethane/methanol (20:1) gave a dark brown solid, which was washed with ethyl acetate and filtered to afford 10.5 g (43.9 mmol, 59%) of the title compound as a pale brown solid.

MS (FAB) m/z: 240 (M+1).

$^1$H-NMR (DMSO-d$_6$) δ: 2.34 (3H, s), 3.80 (3H, s), 7.70 (2H, br s), 7.83 (1H, s), 7.85 (1H, s).

Step 5. methyl 5-amino-6-chloro-2-methylimidazo[1,2-a]pyridine-8-carboxylic acid A mixture of methyl 5-amino-6-chloro-2-methylimidazo[1,2-a]pyridine-8-carboxylate (Example 2, Step 4, 10.5 g, 43.9 mmol,) and 1 N lithium hydroxide (87.7 mL, 87.7 mmol) in methanol (100 mL) was stirred under reflux for 1 h. After removal of the solvent in vacuo, the residue was suspended with water and treated with 2 N hydrochloric acid to adjust to pH 4. The resulting solid was filtered, washed with water and diethyl ether and dried in vacuo with heating to give 9.5 g (42.2 mmol, 96%) of the title compound as a brown solid.

MS (EI) m/z: 225 (M$^+$).

$^1$H-NMR (DMSO-d$_6$) δ: 2.38 (3H, s), 7.88 (1H, s), 7.92 (1H, s), 8.00 (2H, br s). A signal due to COOH was not observed.

Step 6. 5-amino-6-chloro-N-{[1-(3,3-dimethyl-2-oxobutyl)piperidin-4-yl]methyl}-2-methylimidazo[1,2-a]pyridine-8-carboxamide The title compound was prepared according to the procedure described in the step 5 in Example 1 (METHOD A) from 5-amino-6-chloro-2-methylimidazo[1,2-a]pyridine-8-carboxylic acid (Example 2, Step 5) and 1-[4[(aminomethyl)piperidin-1-yl]-3,3-dimethylbutan-2-one (Example 1, METHOD A, Step 5).

MS (ESI+) m/z: 420 (M+1).

m.p.: 198° C.

IR (KBr) ν: 3302, 3148, 2920, 1713, 1638, 1605, 1560, 1545, 1514, 1433, 1323, 1286, 1265, 1231, 1065, 721 cm$^{-1}$.

$^1$H-NMR (CDCl$_3$) δ: 1.15 (9H, s), 1.45–1.73 (3H, m), 1.79–1.83 (2H, m), 2.01–2.07 (2H, m), 2.44 (3H, s), 2.90–2.94 (2H, m), 3.36 (2H, s), 3.43–3.48 (2H, m), 5.06 (2H, s), 7.15 (1H, s), 8.17 (1H, s), 10.11 (1H, br).

Anal. Calcd. for $C_{21}H_{30}ClN_5O_2 \cdot 0.05H_2O$: C, 59.93; H, 7.21; N, 16.64. Found: C, 59.58; H, 7.12; N, 16.36.

Example 3

5-amino-n-{[1-(3,3-dimethyl-2-oxobutyl)piperidin-4-yl]methyl}-2-methylimidazo[1,2-a]pyridine-8-carboxamide A mixture of 5-amino-6-chloro-N-{[1-(3,3-dimethyl-2-oxobutyl)piperidin-4-yl]methyl}-2-methylimidazo[1,2-a]pyridine-8-carboxamide (Example 2, Step 6, 300 mg, 0.71 mmol), 10% palladium on carbon (150 mg) and ammonium formate (450 mg, 7.1 mmol) in methanol (10 mL) was stirred at room temperature for 24 h. Another 100 mg of palladium on carbon was added and the stirring was continued for 23 h. The mixture was filtered and the filtrate was concentrated. The residue was treated with 25% aqueous ammonia (10 mL), extracted with dichloromethane (20 mL×2) and washed with brine (10 mL). Removal of the solvent and purification by column chromatography on basic silica gel eluting with ethyl acetate/hexane (5:1) gave 209 mg (0.54 mmol, 76%) of the title compound as a pale yellow amorphous powder.

MS (ESI+) m/z: 386 (M+1).

IR (KBr) ν: 3333, 3190, 2930, 1715, 1645, 1558, 1518, 1433, 1319, 1292 $cm^{-1}$.

$^1$H-NMR (CDCl$_3$) δ: 1.15 (9H, s), 1.47–1.88 (5H, m), 2.01–2.09 (2H, m), 2.46 (3H, s), 2.91–2.95 (2H, m), 3.37 (2H, s), 3.44–3.48 (2H, m), 4.65 (2H, br s), 6.12 (1H, d, J=7.8 Hz), 7.13 (1H, s), 8.12 (1H, d, J=7.8 Hz), 10.21 (1H, br).

Anal. Calcd. for $C_{21}H_{31}N_5O_2 \cdot 0.7H_2O$: C, 63.35; H, 8.20; N, 17.59. Found: C, 63.32; H, 8.38; N, 17.21.

Example 4

5amino6chloro-n-{[1-(3,3-dimethyl-2-oxobutyl)piperidin-4-yl]methyl}-2-ethylimidazo[1,2-a]pryidine-8-carboxamide Step 1. methyl 5-amino-6-chloro-2-ethylimidazo[1,2-a]pyridine-8-carboxylate The title compounds were prepared according to the procedure described in the step 4 in Example 2 from methyl 2,6-diamino-5-chloro-3-pyridinecarboxylate (Example 2, Step 3) and 1-bromo-2-butanone.

MS (EI) m/z: 253 (M$^+$).

$^1$H-NMR (DMSO-d$_6$) δ: 1.27 (3H, t, J=7.5 Hz), 2.72 (2H, q, J=7.5 Hz), 3.80 (3H, s), 7.72 (2H, s), 7.86 (1H, s), 7.87 (1H, s).

Step 2. 5-amino-6-chloro-2-ethylimidazo[1,2-a]pyridine-8-carboxylic acid

The title compound was prepared, according to the procedure described in the step 5 in Example 2, from methyl 5-amino-6-chloro-2-ethylimidazo[1,2-a]pyridine-8-carboxylate (Example 4, Step 1).

MS (EI) m/z: 239 (M$^+$).

$^1$H-NMR (DMSO-d$_6$) δ: 1.27 (3H, t, J=7.2 Hz), 2.74 (2H, q, J=7.2 Hz), 7.88 (1H, s), 7.95 (1H, s). A signal due to COOH was not observed.

Step 3. tert-butyl 4-({[(5-amino-6-chloro-2-ethylimidazo[1,2-a]pyridin-8-yl)carbonyl]amino}methyl)piperidine-1-carboxylate A mixture of 5-amino-6-chloro-2-ethylimidazo[1,2-a]pyridine-8-carboxylic acid (Example 4, Step 2, 10.00 g, 41.72 mmol), tert-butyl 4-(aminomethyl)piperidine-1-carboxylate (J. Prugh, L. A. Birchenough and M. S. Egbertson, Synth. Commun., 1992, 22, 2357–60, 15.20 g, 70.93 mmol), DEPC (10.76 mL, 70.93 mmol) and diisopropylethylamine (18.17 mL, 104.4 mmol) in N,N-dimethylformamide (267 mL) was stirred at room temperature for 43 h. The solvent was removed by evaporation. The residue was basified with aqueous sodium bicarbonate (40 mL), and extracted with dichloromethane (5×100 mL). The combined extract was washed with brine, dried over magnesium sulfate, and concentrated in vacuo. Flash chromatography of the residue eluting with dichloromethane/methanol (100:1 to 20:1) afforded 19.08 g (90%) of the title compound as a yellow oil.

$^1$H-NMR (CDCl$_3$) δ: 1.35 (3H, t, J=7.6 Hz), 1.45 (9H, s), 1.88–1.28 (5H, m), 2.88–2.64 (2H, m), 3.52–3.38 (2H, m), 4.30–3.97 (4H, m), 5.17 (2H, br s), 7.21 (1H, s), 8.19 (1H, s), 10.21 (1H, by).

Step 4. 5-amino-6-chloro-2-ethyl-N-(piperidin-4-ylmethyl)imidazo[1,2-a]pyridine-8-carboxamide To a stirred solution of tert-butyl 4-({[(5-amino-6-chloro-2-ethylimidazo[1,2-a]-pyridin-8-yl)carbonyl]amino}methyl)piperidine-1-carboxylate (Example 4, Step 3, 13.71 g, 31.44 mmol) in 10% hydrochloric acid methanol solution (314 mL) was added concentrated hydrochloric acid (10 mL). After stirring at room temperature for 26 h, the mixture was concentrated to about 50 mL in vacuo. The residue was basified with an excess of sodium carbonate and then insoluble material was filtered off. The filtrate was concentrated azeotropically with ethanol and diluted with a mixture of dichloromethane and methanol (5:1, 200 mL). The formed inorganic solid was filtered off again. The filtrate was concentrated in vacuo to give a pale yellow amorphous powder, which was crystallized from ethanol to afford 4.79 g (45%) of the title compound as an off-white solid. Furthermore, 5.09 g (48%) of the compound was obtained from the mother liquid.

MS (ESI) m/z: 336 (M+H)$^+$, 334 (M−H)$^-$.

m.p. (TG/DTA): 153° C.

IR (KBr) ν: 3387, 3300, 3188, 2964, 1639, 1605, 1562, 1514 $cm^{-1}$.

$^1$H-NMR (DMSO-d$_6$) δ: 1.30–0.90 (2H, m), 1.30 (3H, t, J=7.6 Hz), 1.74–1.50 (3H, m), 2.55–2.36 (2H, m), 2.75 (2H, q, J=7.6 Hz), 3.04–2.86 (2H, m), 3.27 (2H, t, J=5.9 Hz), 7.86 (1H, s), 7.94 (1H, s), 10.05–9.94 (1H, m).

Anal. Calcd. for $C_{16}H_{22}ClN_5O_{2.5}H_2O \cdot 0.8EtOH$: C, 50.70; H, 7.49; N, 16.80. Found: C, 50.57; H, 7.27; N, 16.80.

Step 5. 5-amino-6-chloro-N-{[1-(3,3-dimethyl-2-oxobutyl)piperidin-4-yl]methyl}-2-ethylimidazo[1,2-a]pyridine-8-carboxamide To a stirred mixture of 5-amino-6-chloro-2-ethyl-N-(piperidin-4-ylmethyl)imidazo[1,2-a]pyridine-8-carboxamide (Example 4, Step 4, 150 mg, 0.446 mmol) and 1-bromo-3,3-dimethylbutan-2-one (72 μL, 0.670 mmol) in N,N-dimethylformamide (4.4 mL) were added sodium iodide (67 mg, 0.670 mmol) and triethylamine (0.156 mL, 1.12 mmol). The reaction mixture was stirred at 70° C. for 76 h. After removal of solvent, the residue was dissolved in ethyl acetate (100 mL), and washed with aqueous sodium bicarbonate (5 mL) and brine. The organic layer was dried over magnesium sulfate and concentrated in vacuo. Flash column chromatography (NH-silica gel) of the residue eluting with hexane/ethyl acetate (9:1 to 1:1) afforded a pale brown solid, which was recrystallized from ethyl acetate to afford 62 mg (32%) of the title compound as off-white solid.

MS (EI) m/z: 433 (M)$^+$.

m.p. (TG/DTA): 206° C.

IR (KBr) ν: 3144, 2964, 2930, 1715, 1636, 1605, 1558 $cm^{-1}$.

$^1$H-NMR (CDCl$_3$) δ: 1.15 (9H, s), 1.36 (3H, t, J=7.5 Hz), 1.75–1.40 (3H, m), 1.88–1.77 (2H, m), 2.10–1.97 (2H, m), 2.83 (2H, q, J=7.5 Hz), 2.97–2.87 (2H, m), 3.36 (2H, s), 3.45 (2H, t, J=6.2 Hz), 4.93 (2H, bvs), 7.12 (1H, s), 8.20 (1H, s).

Anal. Calcd. for C$_{22}$H$_{32}$ClN$_5$O$_2$: C, 60.89; H, 7.43; N, 16.14. Found: C, 60.99; H, 7.50; N, 16.22.

Example 5

5amino6chloro2-ethyl-n-{[1-(3-hydroxy-3-methyl-2-oxobutyl)piperidin-4-yl]methyl}imidazo[1,2-a]pryidine-8-carboxamide To a stirred mixture of 5-amino-6-chloro-2-ethyl-N-(piperidin-4-ylmethyl)imidazo[1,2-a]pyridine-8-carboxamide (Example 4, Step 4, 350 mg, 1.042 mmol) and triethylamine (0.36 mL, 2.61 mmol) in tetrahydrofuran (10 mL) was added 1-bromo-3-hydroxy-3-methylbutan-2-one (G. Bertram; A. Scherer; W. Steglich; W. Weber, *Tetrahedron Lett.*, 1996, 37, 7955–7958, 296 mg, 1.77 mmol). The reaction mixture was refluxed for 62 h and then cooled. After basified with aqueous potassium carbonate (15 mL), the solvent was removed by azeotropically evaporating with ethanol. The residue was dissolved in a mixture of dichloromethane/methanol (5:1, 10 mL) and an insoluble solid was filtered off. The filtrate was concentrated. Flash chromatography (NH-silica gel) of the residue eluting with dichloromethane/methanol (200:0 to 200:1) afforded a brown amorphous powder, which was crystallized from ethyl acetate to give 210 mg (46%) of the title compound as a pale brown solid.

MS (ESI) m/z: 436 (M+H)$^+$, 434 (M−H)$^-$.

m.p. (TG/DTA): 175° C.

IR (KBr) ν: 3179, 2922, 1726, 1636, 1601, 1558 cm$^{-1}$.

$^1$H-NMR (CDCl$_3$) δ: 1.350 (6H, s), 1.352 (3H, t, J=7.5 Hz), 1.94–1.40 (5H, m), 2.22–2.09 (2H, m), 2.83 (2H, q, J=7.5 Hz), 2.99–2.88 (2H, m), 3.36 (2H, s), 3.46 (2H, t, J=7.5 Hz), 5.04 (2H, bvs), 7.16 (1H, s), 8.19 (1H, s), 10.20 (1H, by).

Anal. Calcd. for C$_{21}$H$_{30}$ClN$_5$O$_3$·0.2H$_2$O: C, 57.38; H, 6.97; N, 15.93. Found: C, 57.74; H, 7.06; N, 15.60.

Example 6

5amino6chloro2-ethyl-n-{[1-(4-hydroxy-3,3-dimethyl-2-oxobutyl)piperidin-4-yl]methyl}imidazo[1,2-a]pryidine-8-carboxamide Step 1. 4-bromo-2,2-dimethyl-3-oxobutyl trifluoroacetate To a stirred solution of 2,2-dimethyl-3-oxobutyl trifluoroacetate (W. C. Lumma, Jr. and O. H. Ma, *J. Org. Chem.*, 1970, 35, 2391–2393, 8.45 g, 39.8 mmol) in chloroform (26 mL) was added bromine (1.93 mL, 37.8 mmol) in chloroform (14 mL) dropwise at room temperature. The resulting mixture was stirred at room temperature for 1 h. The mixture was poured into crashed ice/water, and aqueous Na$_2$S$_2$O$_3$ (20 mL) and aqueous NaH$_2$PO$_4$ (40 mL) were added. After the mixture was extracted with chloroform (3×30 mL), the extract was dried over magnesium sulfate and concentrated. Distillation of the residue at 99–102° C. under diminished pressure (3.4 mmHg) afforded 3.58 g (30%) of the title compound as colorless oil.

$^1$H-NMR (CDCl$_3$) δ: 1.35 (6H, s), 4.14 (2H, s), 4.40 (2H, s).

Step 2. 5-amino-6-chloro-2-ethyl-N-{[1-(4-hydroxy-3,3-dimethyl-2-oxobutyl)piperidin-4-yl]methyl}imidazo[1,2-a]pyridine-8-carboxamide A mixture of 5-amino-6-chloro-2-ethyl-N-(piperidin-4-ylmethyl)imidazo[1,2-a]-pyridine-8-carboxamide (Example 4, step 4, 530 mg, 1.57 mmol) and 4-bromo-2,2-dimethyl-3-oxobutyl trifluoroacetate (Example 6, step 1, 777 mg, 2.67 mmol) in methanol (15 mL) was stirred at room temperature for 5 days. The reaction mixture was concentrated in vacuo. The residue was basified with aqueous potassium carbonate (20 mL) and extracted with dichloromethane (3×30 mL). The combined extract was washed with brine, dried over magnesium sulfate, and evaporated. Flash column chromatography (NH-silica gel) of the residue eluting with dichloromethane/methanol (200:1 to 50:1) afforded a white solid. This was recrystallized from ethanol to afford 173 mg (25%) of the title compound as a white solid.

MS (ESI) m/z: 450 (M+H)$^+$, 448 (M−H)$^-$.

m.p. (TG/DTA): 177° C.

IR (KBr) ν: 3179, 2930, 1713, 1638, 1607, 1558 cm$^{-1}$.

$^1$H-NMR (CDCl$_3$) δ: 1.14 (6H, s), 1.35 (3H, t, J=7.6 Hz), 1.93–1.40 (5H, m), 2.21–2.08 (2H, m), 2.82 (2H, q, J=7.6 Hz), 2.98–2.88 (2H, m), 3.22 (2H, s), 3.43 (2H, t, J=6.4 Hz), 3.54 (2H, s), 4.94 (2H, br s), 7.11 (1H, s), 8.19 (1H, s), 10.19 (1H, br s).

Anal. Calcd. for C$_{22}$H$_{32}$ClN$_5$O$_3$: C, 58.72; H, 7.17; N, 15.56. Found: C, 58.50; H, 7.25; N, 15.47.

Example 7

5amino6chloro2-ETHYL-N-{[1-(2-oxy-2-piperidin-1-ylethyl)piperidin-4-yl]methyl}imidazo[1,2-a]pryidine-8-carboxamide The tilte compound was prepared according to the procedure described in the step 5 of Example 4 from 5-amino-6-chloro-2-ethyl-N-(piperidin-4-ylmethyl)imidazo[1,2-a]pyridine-8-carboxamide (Example 4, Step 4) and 1-(chloroacetyl)piperidine (A. Ohta; Y. Tonomura; J. Sawamura; N. Sato; H. Akiike; M. Ikuta, M. Shimazaki, *Heterocycles*, 1991, 32, 965–73).

MS (ESI) m/z: 461 (M+H)$^+$, 459 (M−H)$^-$.

m.p. (TG/DTA): 210° C.

IR (KBr) ν: 3142, 2932, 2851, 1638, 1558, 1545 cm$^{-1}$.

$^1$H-NMR (CDCl$_3$) δ: 1.33 (3H, t, J=7.5 Hz), 1.76–1.34 (9 h, m), 1.90–1.78 (2H, m), 2.15–2.00 (2H, m), 2.80 (2H, q, J=7.5 Hz), 2.97–2.86 (2H, m), 3.15 (2H, s), 3.45 (2H, t, J=6.2 Hz), 3.59–3.47 (4H, m), 5.15 (2H, bvs), 7.19 (1H, s), 8.18 (1H, s), 10.17 (1H, br s).

Anal. Calcd. for C$_{23}$H$_{33}$ClN$_6$O$_2$·0.4H$_2$O: C, 59.00; H, 7.28; N, 17.95. Found: C, 59.21; H, 7.34; N, 17.80.

Example 8

5amino6chloro2-ethyl-N-{[1-(2-morpholin-4-YL-2-oxoethyl)piperidin-4-yl]methyl}imidazo[1,2-a]pryidine-8-carboxamide The title compound was prepared according to the procedure described in the step 5 of Example 4 from 5-amino-6-chloro-2-ethyl-N-(piperidin-4-ylmethyl)imidazo[1,2-a]pyridine-8-carboxamide (Example 4, Step 4) and 4-(chloroacetyl)morpholine (B. G. Hazra; V. S. Pore; S. P. Maybhate, *Org. Prep. Proced. Int.*, 1989, 21, 355–8).

MS (ESI) m/z: 463 (M+H)$^+$, 461 (M−H)$^-$.

m.p. (TG/DTA): 217° C.

IR (KBr) ν: 3179, 2922, 1638, 1558, 1545 cm$^{-1}$.

$^1$H-NMR (CDCl$_3$) δ: 1.35 (3H, t, J=7.5 Hz), 1.92–1.37 (5H, m), 2.15–2.05 (2H, m), 2.81 (2H, q, J=7.5 Hz), 2.96–2.83 (2H, m), 3.15 (2H, s), 3.45 (2H, t, J=6.2 Hz), 3.74–3.56 (8H, m), 5.08 (2H, br s), 7.17 (1H, s), 8.19 (1H, s), 10.17 (1H, br s).

Anal. Calcd. for $C_{22}H_{31}ClN_6O_3$: C, 57.07; H, 6.75; N, 18.15. Found: C, 57.03; H, 6.94; N, 18.15.

Example 9

5amino6chloro2-ethyl-N-{[1-(3-morpholin-4-YL-3-oxopropyl)piperidin-4-yl]methyl}IMIDAZO[1,2-a]pryidine-8-carboxamide To a stirred mixture of 5-amino-6-chloro-N-(piperidin-4-ylmethyl)imidazo[1,2-a]pyridine-8-carboxamide (Example 4, Step 4, 400 mg, 1.19 mmol) and 4-(3-chloro-propanoyl)morpholine (G. Mattalia,; C. Serafini; U. Bucciarelli, *Farmaco, Ed. Sci.*, 1976, 31, 457–67., 529 mg, 2.98 mmol) in N,N-dimethylformamide (5 mL) were added potassium carbonate (576 mg, 4.17 mmol) and sodium iodide (446 mg, 2.98 mmol). After stirring at 90° C. for 48 h, the reaction mixture was cooled to room temperature. The mixture was evaporated and the obtained residue was partitioned between dichloromethane (30 mL) and water (20 mL). The mixture was extracted with dichloromethane (2×30 mL). The combined extract was washed with brine, dried over magnesium sulfate, and concentrated in vacuo. Flash column chromatography (NH-silica gel) of the residue eluting with dichloromethane/methanol (100:1 to 20:1) afforded a yellow amorphous powder, which was crystallized from ethyl acetate/ethanol to give 359 mg (63%) of the title compound as a pale brown solid.

MS (ESI) m/z: 477 (M+H)$^+$, 475 (M−H)$^−$.

m.p. (TG/DTA): 189° C.

IR (KBr) ν: 3196, 2912, 1649–1614, 1558 cm$^{-1}$.

$^1$H-NMR (CDCl$_3$) δ: 1.36 (3H, t, J=7.5 Hz), 1.50–1.30 (3H, m), 2.10–1.80 (4H, m), 2.59–2.48 (2H, m), 2.75–2.65 (2H, m), 2.83 (2H, q, J=7.5 Hz), 3.00–2.89 (2H, m) 3.52–3.41 (4H, m), 3.70–3.58 (6H, m), 5.04 (2H, br s), 7.16 (1H, s), 8.19 (1H, s) 10.17(1H, br s).

Anal. Calcd. for $C_{23}H_{33}ClN_6O_3 \cdot 0.2C_4H_8O_2$: C, 57.79; H, 7.05; N, 16.99. Found: C, 58.09; H, 7.26; N, 16.91.

Example 10

5amino-n-({1-[2-(4-tert-butylphenyl)ethyl]piperidin-4-yl}methyl)-6chloro2-ethylimidazo[1,2-a]pryidine-8-carboxamide The title compound was prepared according to the procedure described in the step 5 of Example 4 from 5-amino-6-chloro-2-ethyl-N-(piperidin-4-ylmethyl)imidazo[1,2-a]pyridine-8-carboxamide (Example 4, Step 4) and 1-(2-bromoethyl)-4-tert-butylbenzene (*Chem. Abstr.* 1963, 58, 5570f).

MS (ESI+) m/z: 496(M+1).

m.p.: 220° C.

IR (KBr) ν: 3302, 3142, 3090, 2964, 2934, 1638, 1607, 1558, 1543, 1514, 1435, 1364, 1335, 1269, 1231 cm$^{-1}$.

$^1$H-NMR (CDCl$_3$) δ: 1.30 (9H, s), 1.36 (3H, t, J=7.5 Hz), 1.43–1.53 (2H, m), 1.60–1.76 (1H, m), 1.85–1.89 (2H, m), 1.99–2.07 (2H, m), 2.55–2.61 (2H, m), 2.76–2.87 (4H, m), 3.02–3.06 (2H, m), 3.45–3.49 (2H, m), 5.03 (2H, br s), 7.12–7.15 (3H, m), 7.29–7.31 (2H, m), 8.20 (1H, s), 10.19 (1H, br).

Anal. Calcd. for $C_{28}H_{38}ClN_5O$: C, 67.79; H, 7.72; N, 14.12. Found: C, 67.92; H, 7.89; N, 14.17.

Example 11

5amino6chloro2-ethyl-n-{[1-(2-[(methylsulfonyl)amino]ethyl}piperidin-4-yl)methyl]IMIDAZO[1,2-a]pryidine-8-carboxamide The title compound was prepared according to the procedure described in the step 5 of Example 1 from 5-amino-6-chloro-2-ethylimidazo[1,2-a]pyridine-8-carboxilic acid (Example 4, Step 2) and N-{2-[4-(aminomethyl)piperidin-1-yl]ethyl}methanesulfonamide (M. opez-Rodriguez; B. Benhamu; A. Viso; M. J. Morcillo; M. Murcia; L. Orensanz; M. J. Alfaro; M. I. Martin, *Bioorg. Med. Chem.*, 1999, 7, 2271–2281.)

MS (ESI+) m/z: 458 (M+H)$^+$ m.p. (TG/DTA): 190° C.

IR (KBr) ν: 3429, 3342, 3152, 2930, 1705, 1645, 1607, 1556 cm$^{-1}$.

$^1$H-NMR (CDCl$_3$ including 1 drop of CD$_3$OD) δ: 1.92–1.30 (8H, m), 2.11–1.97 (2H, m), 2.58–2.48 (2H, m), 2.95–2.77 (4H, m), 2.96 (3H, s), 3.23–3.14 (2H, m), 3.50–3.40 (2H, m), 7.25 (1H, s), 8.05 (1H, br s), 8.16 (1H, s), 10.26 (1H, br s).

Anal. Calcd. for $C_{19}H_{29}ClN_6O_3S \cdot 0.2C_4H_8O_2$: C, 50.11; H, 6.50; N, 17.71. Found: C, 50.30; H, 6.25; N, 17.52.

Example 12

5amino6chloro-n-{[1-(2-hydroxy-3,3-dimethylbutyl)piperidin-4-yl]methyl}-2-methylimidazo[1,2-a]pryidine-8-carboxamide To a suspension of 5-amino-6-chloro-N-{[1-(3,3-dimethyl-2-oxobutyl)piperidin-4-yl]methyl}-2-methylimidazo[1,2-a]pyridine-8-carboxamide (Example 2, Step 3, 300 mg, 0.71 mmol) in methanol (10 mL) was added sodium borohydride (54 mg, 1.43 mmol) at 0° C. The mixture was stirred at room temperature for 2 days and the excess reagent was quenched with water (5 mL). The solution was basified with aqueous ammonia and extracted with dichloromethane (3×10 mL). After dryness, removal of solvent gave the residual solid, which was washed with hexane to afford the title compound (257 mg, 85%) as a white amorphous solid.

MS (ESI+) m/z: 422(M+1).

IR (KBr) ν: 3470, 3304, 3148, 2951, 1638, 1605, 1560, 1545, 1512, 1435, 1364, 1323, 1285, 1267, 1231 cm$^{-1}$.

$^1$H-NMR (CDCl$_3$) δ: 0.90 (9H, s), 1.27–1.90 (6H, m), 2.27–2.37 (3H, m), 2.47 (3H, s), 2.78–2.82 (1H, m), 3.04–3.08 (1H, m), 3.30–3.36 (1H, m), 3.42–3.47 (2H, m), 4.97 (2H, br s), 7.14 (1H, s), 8.20 (1H, s), 10.11 (1H, br).

Anal. Calcd. for $C_{21}H_{32}ClN_5O_2 \cdot 0.25C_6H_{12}$: C, 59.90; H, 7.69; N, 16.51. Found: C, 60.21; H, 7.99; N, 16.22.

Example 13

5amino6chloro2-ethyl-n-{[1-(2-hydroxybutyl)piperidin-4-yl]methyl}imidazo[1,2-a]pryidine-8-carboxamide oxalate (2:1)

Step 1. 1-(2-oxobutyl)piperidine-4-carboxamide

The title compound was prepared according to the procedure described in the step 5 of Example 4 from isonipecotamide and 1-bromobutan-2-one.

MS (ESI+) m/z: 199 (M+H)$^+$

1H-NMR (CDCl$_3$) δ:1.06 (3H, t, J=7.3 Hz), 1.94–1.74 (4H, m), 2.22–2.06 (3H, m). 2.47 (2H, q, J=7.3 Hz), 2.95–2.85 (2H, m), 3.17 (2H, s), 5.50–5.20 (2H, m)

Step 2. 1-[4-(aminomethyl)piperidin-1-yl]butan-2-ol

To a stirred mixture of 1-(2-oxobutyl)piperidine-4-carboxamide (Example 13, Step 1, 1.60 g, 8.07 mmol) in tetrahydrofuran (200 mL) was added portionwise lithium aluminum hydride (920 mg, 24.21 mmol) at room temperature. The resulting mixture was refluxed for 5 h and cooled to room temperature. The mixture was treated with water (1.8 mL), 2N aqueous sodium hydroxide (3.6 mL) and water (1.8 mL). The mixture was filtered through a pad of Celite and the filtrate was concentrated in vacuo to afford 1.64 g (97%) of the title compound as colorless oil.

MS (ESI+) m/z: 187 (M+H)+.

$^1$H-NMR (CDCl$_3$) δ: 0.97 (3H, t, J=7.5 Hz), 2.40–1.10 (9H, m), 2.58 (2H, d, J=6.0 Hz), 2.87–2.72 (2H, m), 3.09–2.95 (2H, m), 3.64–3.52 (1H, m).

Step 3. 5-amino-6-chloro-2-ethyl-N-{1[1-(2-hydroxybutyl) piperidin-4-yl]methyl}-imidazo[1,2-a]pyridine-8-carboxamide The tilte compound (free base) was prepared according to the procedure described in the step 5 of Example 1 from 5-amino-6-chloro-2-ethylimidazo[1,2-a]pyridine-8-carboxilic acid (Example 4, Step 2) and 1-[4-(aminomethyl) piperidin-1-yl]butan-2-ol (Example 13, Step 2).

$^1$H-NMR (CDCl$_3$) δ: 0.97 (3H, t, J=7.4 Hz), 1.33 (3H, dt, J=7.1, 0.7 Hz), 2.88–1.25 (13H, m), 3.09–2.96 (2H, m), 3.66–3.41 (3H, m), 5.15 (2H, br s), 7.21 (1H, s), 8.20 (1H, s), 10.25–10.09 (1H, m).

Step 4. 5-amino-6-chloro-2-ethyl-N-{[1-(2-hydroxybutyl) piperidin-4-yl]methyl}-imidazo[1,2-a]pyridine-8-carboxamide oxalate (2:1)

5-amino-6-chloro-2-ethyl-N-{[1-(2-hydroxybutyl) piperidin-4-yl]methyl}-imidazo[1,2-a]pyridine-8-carboxamide (Example 13, Step 3, 79 mg, 0.19 mmol) was dissolved in methanol (3 mL) and acidified with oxalic acid (17.4 mg, 0.13 mmol) in methanol (2 mL). The mixture was then concentrated and a white precipitate was washed with ethyl acetate to afford (92 mg, 80%) of the title compound.

MS (ESI) m/z: 408 (M+H)+, 406 (M−H)−.

m.p. (TG/DTA): 179° C. (decomposition).

IR (KBr) v: 3335, 2964, 2731, 1717, 1705, 1645, 1601, 1559 cm$^{-1}$.

$^1$H-NMR (DMSO-d$_6$) δ: 0.88 (3H, t, J=7.2 Hz), 1.30 (3H, t, J=7.5 Hz), 2.75 (2H, q, J=7.5 Hz), 4.50–1.10 (15H, m), 5.04–4.89 (1H, m), 7.64 (1H, s), 7.87 (1H, s), 7.93 (1H, s), 9.99 (1H, br s).

Anal. Calcd. for C$_{21}$H$_{31}$ClN$_5$O$_4$.0.5C$_4$H$_8$O$_2$.3H$_2$O: C, 50.46; H, 7.62; N, 11.77 Found: C, 50.25; H, 7.30; N, 11.75.

Example 14

5amino6chloro2-ethyl-n-{[(1-(2-hydroxy-2-methylpropyl)piperidin-4-yl]methyl}imidazo[1,2-a] pryidine-8-carboxamide A solution of 5-amino-6-chloro-2-ethyl-N-(piperidin-4-ylmethyl)imidazo[1,2-a]-pyridine-8-carboxamide (Example 4, Step 4, 100 mg, 0.298 mmol) and 2,2-dimethyloxirane (64 mg, 0.893 mmol) in methanol (1.2 mL) was stirred overnight at room temperature. After evaporation, flash column chromatography (NH-silica gel) of the residue eluting with dichloromethane/methanol (only dichloromethane to 200:1) quantitatively afforded a white solid. This was recrystallized from diethyl ether to afford 89 mg (74%) of the title compound as a white solid.

MS (ESI) m/z: 408 (M+H)+, 406 (M−H)−.

m.p. (TG/DTA): 216° C.

IR (KBr) v: 3146, 2964, 2922, 1636, 1607, 1558 cm−.

$^1$H-NMR (CDCl$_3$) δ: 1.14 (6H, s), 1.36 (3H, t, J=7.5 Hz), 1.85–1.40 (5H, m), 2.30 (2H, s), 2.40–2.31 (2H, m), 2.83 (2H, q, J=7.5 Hz), 2.98–2.88 (2H, m), 3.34 (1H br s), 3.46 (2H, t, J=6.1 Hz), 5.00 (2H, br s), 7.15 (1H, s), 8.20 (1H, s), 10.19 (1H, br s).

Anal. Calcd. for C$_{20}$H$_{30}$ClN$_5$O$_2$: C, 58.89; H, 7.41; N, 17.17. Found: C, 58.63; H, 7.41; N, 17.01.

Example 15

5amino6chloro-n-{[1-(2-hydroxy-2-methylpropyl) piperidin-4-yl]methyl}-2-methylimidazo[1,2-a] pryidine-8-carboxamide Step 1. tert-butyl 4-({[(5-amino-6-chloro-2-methylimidazo [1,2-a]pyridin-8-yl)carbonyl]amino}methyl)piperidine-1-carboxylate The title compound was prepared according to the procedure described in the step 3 of Example 4 from 5-amino-6-chloro-2-methylimidazo[1,2-a]pyridine-8-carboxilic acid (Example 2, Step 5) and tert-butyl 4-(aminomethyl) piperidine-1-carboxylate (J. Prugh, L. A. Birchenough and M. S. Egbertson, *Synth. Commun.*, 1992, 22, 2357–60).

MS (EI) m/z: 421 (M+).

$^1$H-NMR (CDCl$_3$) 6:1.06–1.84 (14H, m), 2.44 (3H, s), 2.58–2.85 (2H, m), 3.45–3.49 (2H, m), 4.00–4.22 (2H, m), 5.84 (2H, s), 7.34 (1H, s), 8.17 (1H, s), 10.17 (1H, br t, J=5.7 Hz).

Step 2. 5-amino-6-chloro-2-methyl-N-(piperidin-4-ylmethyl)imidazo[1,2-a]pyridine-8-carboxamide The title compound was prepared according to the procedure described in the step 4 of Example 4 from tert-butyl 4-({[(5-amino-6-chloro-2-methylimidazo[1,2-a]pyridin-8-yl)carbonyl]amino}methyl)piperidine-1-carboxylate (Example 15, Step 1).

MS (ESI+) m/z: 322(M+1).

$^1$H-NMR (DMSO-d$_6$) δ: 1.35–1.48 (2H, m), 1.81–1.85 (3H, m), 2.38 (3H, s), 2.80–2.88 (2H, m), 3.24–3.39 (4H, m), 7.65 (2H, s), 7.86 (1H, s), 7.93 (1H, s), 8.64 (1H, br s), 9.93 (1H, br t, J=6.0 Hz).

Step 3. 5-amino-6-chloro-N-{1[1-(2-hydroxy-2-methylpropyl)piperidin-4-yl]methyl}-2-methylimidazo[1,2-a]pyridine-8-carboxamide The title compound was prepared according to the procedure described in Example 14 from 5-amino-6-chloro-2-methyl-N-(piperidin-4-ylmethyl)imidazo[1,2-a]pyridine-8-carboxamide (Example 15, Step 2) and 2,2-dimethyloxirane.

MS (ESI+) m/z: 394(M+1).

IR (KBr) v: 3474, 3304, 3148, 2968, 2922, 1638, 1605, 1560, 1545, 1514, 1433, 1381, 1321, 1229, 718 cm$^{-1}$.

$^1$H-NMR (CDCl$_3$) δ:1.15 (6H, s), 1.38–1.80 (5H, m), 2.30–2.38 (4H, m), 2.47 (3H, s), 2.91–2.96 (2H, m), 3.43–3.48 (2H, m), 5.00 (2H, br s), 7.16 (1H, s), 8.20 (1H, s), 10.11 (1H, br).

Anal. Calcd. for C$_{19}$H$_{28}$ClN$_5$O$_2$: C, 57.93; H, 7.16; N, 17.78. Found: C, 58.02; H, 7.10; N, 17.61.

Example 16

5amino6chloro-n-({1-[(2R)-3-hydroxy-2-methylpropyl]piperidin-4-yl}methyl)-2-methylimidazo[1,2-a]pryidine-8-carboxamide Step 1. 5-amino-6-chloro-2-methyl-N-(piperidin-4-ylmethyl)imidazo[1,2-a]pyridine-8-carboxyamide dihydrochloride A mixture of tert-butyl 4-({[(5-amino-6-chloro-2-methylimidazo[1,2-a]pyridin-8-yl)carbonyl]amino}methyl) piperidine-1-carboxylate (Example 15, Step 1, 15.1 g, 35.8 mmol) and conc. hydrochloric acid (5 mL) in 10% hydrochloric acid methanol solution (150 mL) was stirred at room temperature for 12 h. The solvent was removed to 30 mL in vacuo and diethyl ether (100 mL) was added to the residue. Obtained precipitate was collected by filtration and washed with diethyl ether to give 13.9 g (98%) of the title compound as a pale yellow solid.

MS (ESI) m/z: 322(M+1)+.

$^1$H-NMR (DMSO-d$_6$) δ: 1.39–1.53 (2H, m), 1.80–1.91 (3H, m), 2.45 (3H, s), 2.69–2.89 (2H, m), 3.22–3.26 (4H, m), 8.38–9.13 (8H, m).

Step 2,5-amino-6-chloro-N-({1-[(2R)-3-hydroxy-2-methylpropyl]piperidin-4-yl}methyl)-2-methylimidazo[1,2-a]pyridine-8-carboxamide The title compound was prepared according to the procedure described in the step 5 in Example 4 from 5-amino-6-chloro-2-methyl-N-(piperidin-4-ylmethyl)imidazo[1,2-a]pyridine-8-carboxamide dihydrochloride (Example 16, step 1) and (2S)-3-bromo-2-methylpropan-1-ol.

MS (ESI) m/z: 394 (M+H)$^+$, 392(M−H)$^+$.

m.p.: 187° C.

IR (KBr) ν: 3172, 3091, 2922, 1639, 1562, 1544, 1514, 1434, 1323, 1263, 1228, 1033 cm$^{-1}$.

$^1$H-NMR (DMSO-d$_6$) δ: 0.78 (3H, d, J=6.8 Hz), 1.16–1.35 (2H, m), 1.61–1.92 (4H, m), 2.05–2.12 (2H, m), 2.19–2.30 (2H, m), 2.36 (3H, s), 2.78–2.95 (2H, m), 3.20–3.40 (3H, m), 7.57 (1H, s), 7.87 (1H, s), 9.92 (1H, br).

Anal. Calcd. for C19H28ClN5O2.0.5H2O: C, 57.28; H, 7.21; N, 17.58. Found: C, 56.51; H, 7.21; N, 17.56.

Example 17

5amino6chloro2-methyl-n-{[1-(1,3,3-trimethyl-2-oxobutyl)piperidin-4-yl]methyl}imidazo[1,2-a]pryidine-8-carboxamide To a stirred mixture of 5-amino-6-chloro-2-methyl-N-(piperidin-4-ylmethyl)imidazo[1,2-a]pyridine-8-carboxamide dihydrochloride (Example 16, Step 1, 1.36 g, 3.45 mmol), potassium carbonate (1.90 g, 13.8 mmol) and potassium iodide (688 mg, 4.14 mmol) in N,N-dimethylformamide (10 mL) was added 4-bromo-2,2-dimethylpentan-3-one (Katz, J.-J. et al., *Bull. Soc. Chim. Fr.* 1977, 683., 1.0 g, 5.18 mmol) at ambient temperature. After being stirring for 16 h at 80° C., the mixture was partitioned between ethyl acetate and water. After extraction with ethyl acetate, the combined organic layer was dried over magnesium sulfate and concentrated. The residual material was chromatographed on a column of aminopropyl-silica gel eluting with hexane/ethyl acetate (1:3) to give 230 mg (15%) of the title compound as a colorless powder.

MS (ESI) m/z: 434 (M+H)$^+$, 432(M−H)$^+$.

m.p.: 207° C.

IR (KBr) ν: 3149, 3093, 2525, 2868, 1703, 1635, 1602, 1544, 1512, 1434, 1321, 1263, 1228 cm$^{-1}$.

$^1$H-NMR (CDCl$_3$) δ: 1.05 (3H, d, J=6.6 Hz), 1.19 (9H, s), 1.25–1.45 (2H, m), 1.73–1.85 (3H, m), 2.10 (2H, td, J=11.5, 2.4 Hz), 2.45 (3H, s), 2.68–2.85 (2H, m), 3.37–3.46 (2H, m), 3.69 (1H, q, J=6.6 Hz), 5.08 (2H, s), 7.18 (1H, s), 8.17 (1H, s), 10.08 (1H, br).

Anal. Calcd. for C22H32ClN5O2: C, 60.89; H, 7.43; N, 16.14. Found: C, 60.52; H, 7.41; N, 15.89.

Example 18

5amino6chloro2-methyl-N-({1-[2-(1-methylcyclopropyl)-2-oxoethyl]piperidin-4-yl}methyl)imidazo[1,2-a]pryidine-8-carboxamide Step 1,2-bromo-1-(1-methylcyclopropyl)ethanone To a stirred solution of 1-(1-methylcyclopropyl)ethanone (1.96 g, 20 mmol) and acetic acid (0.5 mL) in methanol (20 mL) was added bromine (1 mL, 20 mmol). Then, the mixture was heated at reflux temperature for 4 h. After cooling, the crude mixture was purified by vacuum distillation (65° C./5 mmHg) to give 1.44 g (41%) of the title compound as a colorless oil.

$^1$H-NMR (CDCl$_3$) δ: 0.68 (1H, d, J=6.8 Hz), 0.69 (1H, d, J=6.8 Hz), 1.25 (1H, d, J=6.8 Hz), 1.26 (1H, d, J=6.8 Hz), 1.35 (3H, s), 3.89 (2H, s).

Step 2,5-amino-6-chloro-2-methyl-N-({1-[2-(1-methylcyclopropyl)-2-oxoethyl]piperidin-4-yl}methyl)imidazo[1,2-a]pyridine-8-carboxamide The title compound was prepared according to the procedure described in Example 17 from 5-amino-6-chloro-2-methyl-N-(piperidin-4-ylmethyl)imidazo[1,2-a]pyridine-8-carboxamide dihydrochloride (Example 16, Step 1) and 2-bromo-1-(1-methylcyclopropyl)ethanone (Example 18, Step 1).

MS (ESI) m/z: 418 (M+H)$^+$, 416(M−H)$^+$.

m.p.: 195° C.

IR (KBr) ν: 3418, 3145, 2925, 1699, 1685, 1637, 1604, 1542, 1508, 1431, 1321, 1265, 1232, 1066 cm$^1$.

$^1$H-NMR (CDCl$_3$) δ: 0.68 (1H, d, J=6.8 Hz), 0.69 (1H, d, J=6.8 Hz), 1.25 (1H, d, J=6.8 Hz), 1.26 (1H, d, J=6.8 Hz), 1.36 (3H, s), 1.46–1.59 (2H, m), 1.64–1.83 (5H, m), 2.04 (2H, t, J=11.3 Hz), 2.40 (3H, s), 2.91–2.96 (2H, m), 3.33 (2H, s), 3.33 (2H, s), 3.45 (2H, t, J=6.0 Hz), 7.23 (1H, br), 8.11 (1H, br), 10.14 (1H, br).

Anal. Calcd. for C21H28ClN5O2.0.5H2O: C, 59.72; H, 6.80; N, 16.58. Found: C, 59.70; H, 6.72; N, 16.20.

Example 19

5amino6chloro-n-({1-[(4-hydroxytetrarydro-2h-pyran-4-yl)methyl]piperidin-4-yl}methyl)-2-methylimidazo[1,2-a]pryidine-8-carboxamide The title compound was prepared according to the procedure described in Example 14 from 5-amino-6-chloro-2-methyl-N-(piperidin-4-ylmethyl)imidazo[1,2-a]pyridine-8-carboxamide dihydrochloride (Example 16, Step 1), 1,6-dioxaspiro[2.5]octane, and potassium carbonate.

MS (ESI) m/z: 436 (M+H)$^+$, 434(M−H)$^+$.

m.p.: 213° C.

IR (KBr) ν: 3418, 3188, 2916, 1625, 1604, 1544, 1514, 1431, 1338, 1303, 1265, 1222, 1184, 1066 cm$^1$.

$^1$H-NMR (CDCl$_3$) δ: 1.36–1.81 (10H, m), 2.31 (2H, s), 2.37 (2H, t, J=11.7 Hz), 2.46 (3H, s), 2.86–2.91 (2H, m), 3.45 (2H, t, J=6.2 Hz), 3.49 (2H, s), 3.70–3.84 (4H, m), 5.16 (2H, s), 7.21 (1H, s), 8.18 (1H, s), 10.22 (1H, br).

Anal. Calcd. for C21H30ClN5O3.0.5H2O.CH4O: C, 56.57; H, 7.18; N, 15.34.

Found: C, 56.48; H, 7.50; N, 15.00.

Example 20

5amino6chloro-n-({1-[(4-hydroxytetrahydro-2h-pyran-4-yl)methyl]piperidin-4-yl}methyl)-2-ethylimidazo[1,2-a]pryidine-8-carboxamide The title compound was prepared according to the procedure described in Example 14 from 5-amino-6-chloro-2-ethyl-N-(piperidin-4-ylmethyl)imidazo[1,2-a]pyridine-8-carboxamide (Example 4, Step 4) and 1,6-dioxaspiro[2.5]octane.

MS (ESI) m/z: 450 (M+H)$^+$, 448(M−H)$^+$.

m.p.: 229° C.

IR (KBr) ν: 3188, 2916, 1626, 1545, 1514, 1431, 1339, 1304, 1265, 1223, 1184, 1011, 1085, 1034 cm$^{-1}$.

$^1$H-NMR (CDCl$_3$) δ: 1.36 (3H, t, J=7.5 Hz), 1.40–1.82 (8H, m), 2.31 (2H, s), 2.37 (2H, t, J=11.7 Hz), 2.83 (2H, q, J=7.5 Hz), 2.86–2.91 (2H, m), 3.45 (2H, t, J=6.2 Hz), 3.49 (2H, s), 3.70–3.84 (4H, m), 5.10 (2H, s), 7.18 (1H, s), 8.20 (1H, s), 10.22 (1H, br).

Anal. Calcd. for C22H32ClN5O3.0.2H2O.CH4O: C, 57.77; H, 7.37; N, 14.97.

Found: C, 57.42; H, 7.75; N, 14.67.

Example 21

5amino6chloro-n-{[1-(2-hydroxy-1,1-dimethylethyl)piperidin-4-yl]methyl}-2-methylimidazo[1,2-a]pryidine-8-carboxamide Step 1, ethyl 2-[4-(aminocarbonyl)piperidin-1-yl]-2-methylpropanoate The title compound was prepared according to the procedure described in the Example 17 from piperidine-4-carboxamide and ethyl 2-bromo-2-methylpropanoate.

MS (ESI) m/z: 243 (M+H)$^+$.

$^1$H-NMR (CDCl$_3$) δ:1.28 (3H, t, J=7.1 Hz), 1.30 (6H, s), 1.62–1.79 (3H, m), 1.88–1.93 (2H, m), 2.09–2.24 (2H, m), 2.99–3.05 (2H, m), 4.17 (2H, q, J=7.1 Hz).

Signal due to NH$_2$ was not observed

Step 2, 2-[4-(aminomethyl)piperidin-1-yl]-2-methylpropan-1-ol

The title compound was prepared according to the procedure described in the step 2 in Example 13 from ethyl 2-[4-(aminocarbonyl)piperidin-1-yl]-2-methylpropanoate (Example 21, step 1).

MS (ESI) m/z: 187 (M+H)$^+$.

$^1$H-NMR (CDCl$_3$) δ:1.02 (6H, s), 1.12–1.25 (3H, m), 1.74–1.78 (2H, m), 2.12 (2H, t, J=10.4 Hz), 2.56 (2H, d, J=6.2 Hz), 2.91–3.00 (2H, m), 3.31(2H, s).

Signal due to OH was not observed

Step 3,5-amino-6-chloro-N-{[1-(2-hydroxy-1,1-dimethylethyl)piperidin-4-yl]methyl}-2-methylimidazo[1,2-a]pyridine-8-carboxamide To a stirred suspension of 5-amino-6-chloro-2-methylimidazo[1,2-a]pyridine-8-carboxylic acid (Example 2, step 6, 279 mg, 1.2 mmol) in N,N-dimethylformamide (10 mL) was added 1,1'-carbonyldiimidazole (300 mg, 1.6 mmol) at ambient temperature. Then, the mixture was heated at 60° C. for 3 h. After cooling, a solution of 2-[4-(aminomethyl)piperidin-1-yl]-2-methylpropan-1-ol (241 mg, 1.6 mmol) in N,N-dimethylformamide (2 mL) was added to the reaction mixture. After being stirred for 18 h at room temperature, the mixture was partitioned between dichloromethane and saturated aqueous sodium bicarbonate. After extraction with dichloromethane, the combined organic layer was dried over magnesium sulfate and concentrated. The residue was chromatographed on a column of aminopropyl-silica gel eluting with hexane/ethyl acetate (1:3) to give 183 mg (67%) of the title compound as a pale yellow powder.

MS (ESI) m/z: 394 (M+H)$^+$, 392 (M–H)$^+$.

IR (KBr) ν: 3307, 3066, 2925, 2845, 1643, 1608, 1541, 1508, 1434, 1325, 1267, 1236, 1064 cm$^{-1}$.

$^1$H-NMR (CDCl$_3$) δ: 1.01 (6H, s), 1.28–1.41 (2H, m), 1.55–1.70 (2H, m), 1.84–1.90 (2H, s), 2.15 (2H, t, J=111.3 Hz), 2.46 (3H, s), 2.92–2.97 (2H, m), 3.31 (2H, s), 3.44 (2H, t, J=6.4 Hz), 5.01 (2H, brs), 7.15 (1H, s), 8.20 (1H, s), 10.09 (1H, br).

Anal. Calcd. for C19H28ClN5O2: C, 57.93; H, 7.16; N, 17.78. Found: C, 57.61; H, 7.22; N, 17.58.

Example 22

5amino6chloro2-methyl-n-{[1-(tetrahydro-2h-pyran-4-ylmethyl)piperidin-4-yl]methyl}imidazo[1,2-a]pryidine-8-carboxamide Step 1, {[1-(tetrahydro-2H-pyran-4-ylmethyl)piperidin-4-yl]methyl}amine To a stirred mixture of piperidine-4-carboxamide (1.28 g, 10 mmol), tetrahydro-2H-pyran-4-carboxylic acid (1.43 g, 11 mmol) and diisopropylethylamine (2.09 mL, 11 mmol) in N,N-dimethylformamide was added HBTU (N-[(1H-1,2,3-benzotriazol-1-yloxy)(dimethylamino)methylene]-N-methylmethanaminium hexafluorophosphate, 4.14 g, 11 mmol) at 0° C. After being stirred for 0.5 h at 0° C., the mixture was stirred for 3 h at ambient temperature. Then, the mixture was partitioned between ethyl acetate and water. After extraction with ethyl acetate, the combined organic extract was washed with brine, dried over magnesium sulfate and concentrated. This crude material was dissolved in tetrahydrofuran (50 mL) and added to the mixture of lithium aluminum hydride (1.90 g, 50 mmol) in tetrahydrofuran (50 mL) at 0° C. Then, the mixture was heated at 40° C. and stirred for 5 h. The mixture was cooled to 0° C. and quenched with sodium sulfate decahydrate (3.8 g) and potassium fluoride (9.0 g). After vigorous stirring for 0.5 h, the insoluble materials were filtered off. The filtrate was concentrated to give 2.19 g (99%) of the title compound as a colorless viscous oil.

MS (ESI) m/z: 213 (M+H)$^+$.

$^1$H-NMR (CDCl$_3$) δ: 1.20–1.28 (2H, m), 1.50–1.78 (8H, m), 2.35 (2H, s), 2.55–2.58 (2H, m), 2.82–2.90 (2H, m), 3.30–3.42 (2H, m), 3.49 (2H, s), 3.92–4.00 (2H, m).

Signal due to NH$_2$ was not observed

Step 2,5-amino-6-chloro-2-methyl-N-{[1-(tetrahydro-2H-pyran-4-ylmethyl)piperidin-4-yl]methyl}imidazo[1,2-a]pyridine-8-carboxamide The title compound was prepared according to the procedure described in the step 3 in Example 21 from 5-amino-6-chloro-2-methylimidazo[1,2-a]pyridine-8-carboxylic acid (Example 2, step 6) and {[1-(tetrahydro-2H-pyran-4-ylmethyl)piperidin-4-yl]methyl}amine (Example 22, step 1).

MS (ESI) m/z: 420 (M+H)$^+$, 418(M–H)$^+$.

m.p.: 236° C.

IR (KBr) ν: 3195, 1641, 1546, 1515, 1427, 1323, 1263, 1236 cm$^{-1}$.

$^1$H-NMR (CDCl$_3$) δ: 1.15–1.45 (5H, m), 1.62–1.92 (6H, m), 2.15 (2H, d, J=7.0 Hz), 2.46 (3H, s), 2.82–2.91 (2H, m), 3.30–3.50 (5H, m), 3.90 (2H, dd, J=10.2, 3.3 Hz), 5.16 (2H, brs), 7.15 (1H, s), 8.20 (1H, s), 10.09 (1H, br).

Anal. Calcd. for C21H30ClN5O2: C, 60.06; H, 7.20; N, 16.68. Found: C, 60.34; H, 7.26; N, 16.68.

All publications, including but not limited to, issued patents, patent applications, and journal articles, cited in this application are each herein incorporated by reference in their entirety.

What is claimed is:

1. A compound of the formula (I):

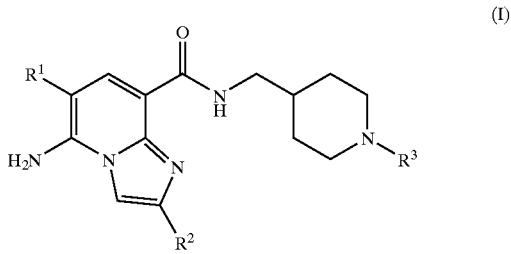

(I)

wherein,

R$_1$ represents hydrogen or halogen;

R$_2$ represents hydrogen, 1 to 6 carbon alkyl, aminocarbonyl, or 1 to 6 carbon mono- or di-alkylaminocarbonyl;

R$_3$ represents 1 to 10 carbon alkyl substituted by 1 to 4 substituents independently selected from: hydroxy, oxo, aminocarbonyl, 1 to 6 carbon mono- or di-alkylaminocarbonyl, 1 to 6 carbon alkylsulfonylamino, 3 to 8 carbon cycloalkyl, 6 to 10 carbon aryl which may be substituted by one or more 1 to 6 carbon alkyl groups, or 5 to 10 membered heterocyclic or heterocycliccarbonyl containing 1 to 4 ring heteroatoms; and wherein the compound may be in the form of a free base, a pharmaceutically acceptable salt, solvate, or hydrate.

2. The compound of claim 1, wherein $R^1$ represents hydrogen or chlorine.

3. The compound of claim 2, wherein $R^2$ represents 1 to 6 carbon alkyl, aminocarbonyl, or 1 to 6 carbon mono- or di-alkylaminocarbonyl.

4. The compound of claim 2, wherein $R_2$ represents 1 to 6 carbon alkyl.

5. The compound of claim 2, wherein $R_2$ represents methyl or ethyl.

6. The compound of claim 1, wherein $R_1$ represents chlorine.

7. The compound of claim 6, wherein $R_2$ represents 1 to 6 carbon alkyl, aminocarbonyl, or 1 to 6 carbon mono- or di-alkylaminocarbonyl.

8. The compound of claim 6, wherein $R_2$ represents 1 to 6 carbon alkyl.

9. The compound of claim 6, wherein $R_2$ represents methyl or ethyl.

10. The compound of claim 1, wherein $R_2$ represents 1 to 6 carbon alkyl, aminocarbonyl, or 1 to 6 carbon mono- or di-alkylaminocarbonyl.

11. The compound of claim 1, wherein $R^2$ represents 1 to 6 carbon alkyl.

12. The compound of claim 1, wherein $R_2$ represents methyl or ethyl.

13. The compound of any one of claims 1–3, or 10, wherein:

$R_3$ represents 1 to 8 carbon alkyl substituted by 1 to 4 substituents independently selected from: hydroxy, oxo, aminocarbonyl, 1 to 6 carbon mono- or di-alkylaminocarbonyl, 1 to 6 carbon alkylsulfonylamino, 3 to 8 carbon cycloalkyl, 6 to 10 carbon aryl which may be substituted by one or more 1 to 6 carbon alkyl groups, or 5 to 7 membered heterocyclic or heterocycliccarbonyl containing 1 to 3 ring heteroatoms.

14. The compound of any one of claims 1–3, or 10, wherein:

$R_3$ represents 1 to 10 carbon alkyl substituted by 1 to 4 substituents independently selected from: hydroxy, oxo. 1 to 6 carbon alkylsulfonylamino, 6 to 10 carbon aryl which may be substituted by one or more 1 to 6 carbon alkyl groups, or 5 to 7 membered hetorocyclic or heterocycliccarbonyl containing 1 to 3 ring heteroatoms.

15. The compound of claim 1, wherein:

$R^3$ represents 1 to 10 carbon alkyl substituted by piperidinonyl or morpholinonyl.

16. A compound selected from:

5-amino-6-chloro-N-{[1-(3,3-dimethyl-2-oxobutyl)piperidin-4-yl]methyl}-2-methylimidazo[1,2-a]pyridine-8-carboxamide;

5-amino-6-chloro-N-{[1-(2-hydroxy-3,3-dimethylbutyl)piperidin-4-yl]methyl}-2-methylimidazo[1,2-a]pyridine-8-carboxamide;

5-amino-6-chloro-2-ethyl-N-{[1-(3-morpholin-4-yl-3-oxopropyl)piperidin-4-yl]methyl}imidazo[1,2-a]pyridine-8-carboxamide;

5-amino-6-chloro-2-ethyl-N-{[1-(2-morpholin-4-yl-2-oxoethyl)piperidin-4-yl]methyl}imidazo[1,2-a]pyridine-8-carboxamide;

5-amino-6-chloro-N-{[1-(3,3-dimethyl-2-oxo-2-butyl)piperidin-4-yl]methyl}-2-ethylimidazo[1,2-a]pyridine-8-carboxamide;

5-amino-6-chloro-2-ethyl-N-{[1-(2-[(methylsulfonyl)amino]ethyl))piperidin-4-yl]]]methyl}imidazo[1,2-a]pyridine-8-carboxamide;

5-amino-6-chloro-2-ethyl-N-{[(1-2-hydroxy-2-methylpropyl)piperidin-4-yl]methyl}imidazo[1,2-a]pyridine-8-carboxamide;

5-amino-6-chloro-N-{[1-(2-hydroxy-2-methylpropyl)piperidin-4-yl]methyl}-2-methylimidazo [1,2-a]pyridine-8-carboxamide;

5-amino-6-chloro-2-ethyl-N-{[1-(4-hydroxy-3,3-dimethyl-2-oxobutyl)piperidin-4-yl]methyl}imidazo[1,2-a]pyridine-8-carboxamide;

5-amino-6-chloro-2-ethyl-N-{[1-(2-hydroxybutyl)piperidin-4-yl]methyl}imidazo[1,2-a]pyridine-8-carboxamide, half oxalate salt; or 5-amino-6-chloro-2-ethyl-N-{[1-(2-oxy-2-piperidin-1-ylethyl)piperidin-4-yl]methyl}imidazo[1,2-a]pyridine-8-carboxamide;

wherein the compound may be in the form of a free base, a pharmaceutically acceptable salt, solvate, or hydrate.

17. A compound selected from:

5-amino-6-chloro-N-{[1-(3,3-dimethyl-2-oxo-2-butyl)piperidin-4-yl]methyl}-2-ethylimidazo[1,2-a]pyridine-8-carboxamide;

5-amino-6-chloro-2-ethyl-N-{[1-(2-[(methylsulfonyl)amino]ethyl))piperidin-4-yl]]]methyl}imidazo[1,2-a]pyridine-8-carboxamide;

5-amino-6-chloro-2-ethyl-N-{[(1-2-hydroxy-2-methylpropyl)piperidin-4-yl]methyl}imidazo[1,2-a]pyridine-8-carboxamide;

5-amino-6-chloro-N-{[1-(2-hydroxy-2-methylpropyl)piperidin-4-yl]methyl}-2-methylimidazo [1,2-a]pyridine-8-carboxamide;

5-amino-6-chloro-2-ethyl-N-{[1-(4-hydroxy-3,3-dimethyl-2-oxobutyl)piperidin-4-yl]methyl}imidazo [1,2-a]pyridine-8-carboxamide;

5-amino-6-chloro-2-ethyl-N-{[1-(2-hydroxybutyl)piperidin-4-yl]methyl}imidazo[1,2-a]pyridine-8-carboxamide, half oxalate salt; or 5-amino-6-chloro-2-ethyl-N-{[1-(2-oxy-2-piperidin-1-ylethyl)piperidin-4-yl]methyl}imidazo[1,2-a]pyridine-8-carboxamide;

wherein the compound may be in the form of a free base, a pharmaceutically acceptable salt, solvate, or hydrate.

18. A pharmaceutical composition comprising a compound of any one of claims 1, 16, or 17, formulated as a pharmaceutical composition alone or in combination with at least one pharmaceutically acceptable carrier.

19. A pharmaceutical composition comprising a compound of claim 13, formulated as a pharmaceutical composition alone or in combination with at least one pharmaceutically acceptable carrier.

20. A method of treating gastroesophageal reflux disease, gastrointestinal disease, gastric motility disorder, upper gut motility disorder, non-ulcer dyspepsia, functional dyspepsia, irritable bowel syndrome, constipation, dyspepsia, esophagitis, comprising administering to a mammal in need thereof an effective amount of a compound of claim 1.

* * * * *